US009764060B2

(12) United States Patent
Nazhat et al.

(10) Patent No.: US 9,764,060 B2
(45) Date of Patent: Sep. 19, 2017

(54) DENSE HYDROGELS

(71) Applicant: THE ROYAL INSTITUTION FOR THE ADVANCEMENT OF LEARNING / MCGILL UNIVERSITY, Montreal (CA)

(72) Inventors: Showan Nazhat, Montreal (CA); Benedetto Marelli, Somerville, MA (US); Chiara Ghezzi, Somerville, MA (US); Neysan Nejat Oliver Kamranpour, Montreal (CA)

(73) Assignee: THE ROYAL INSTITUTION FOR THE ADVANCEMENT OF LEARNING / MCGILL UNIVERSITY, Montreal (CA)

( * ) Notice: Subject to any disclaimer, the term of this patent is extended or adjusted under 35 U.S.C. 154(b) by 0 days.

(21) Appl. No.: 14/420,585

(22) PCT Filed: Aug. 9, 2013

(86) PCT No.: PCT/CA2013/050615
§ 371 (c)(1),
(2) Date: Feb. 9, 2015

(87) PCT Pub. No.: WO2014/022939
PCT Pub. Date: Feb. 13, 2014

(65) Prior Publication Data
US 2015/0182660 A1    Jul. 2, 2015

Related U.S. Application Data

(60) Provisional application No. 61/788,150, filed on Mar. 15, 2013, provisional application No. 61/681,209, filed on Aug. 9, 2012.

(51) Int. Cl.
| | |
|---|---|
| *A61L 27/26* | (2006.01) |
| *B29C 45/00* | (2006.01) |
| *C08J 3/075* | (2006.01) |
| *A61L 27/52* | (2006.01) |
| *A61L 27/54* | (2006.01) |
| *A61L 27/24* | (2006.01) |
| *B01J 13/00* | (2006.01) |

(52) U.S. Cl.
CPC .............. *A61L 27/24* (2013.01); *A61L 27/52* (2013.01); *A61L 27/54* (2013.01); *B01J 13/0069* (2013.01); *C08J 3/075* (2013.01); *A61L 2300/64* (2013.01); *A61L 2400/06* (2013.01); *A61L 2430/02* (2013.01); *A61L 2430/34* (2013.01); *C08J 2389/00* (2013.01)

(58) Field of Classification Search
None
See application file for complete search history.

(56) References Cited

U.S. PATENT DOCUMENTS

| | | | | |
|---|---|---|---|---|
| 3,956,512 A | * | 5/1976 | Higgins ................. | C08L 89/00 426/140 |
| 4,294,241 A | * | 10/1981 | Miyata ................. | A61L 15/325 128/DIG. 8 |
| 4,708,988 A | * | 11/1987 | Tabb ....................... | C08K 5/14 525/193 |
| 6,818,018 B1 | | 11/2004 | Sawhney | |
| 2008/0131473 A1 | | 6/2008 | Brown et al. | |
| 2010/0063174 A1 | * | 3/2010 | Ruberti .................... | C08J 3/075 523/113 |

FOREIGN PATENT DOCUMENTS

| | | |
|---|---|---|
| CA | 2739876 A1 | 4/2010 |
| CN | 102266589 A | 12/2011 |
| WO | 2012116439 A1 | 9/2012 |

OTHER PUBLICATIONS

Zimmerman, Martin; et al; "Capillary pumps for autonomous capillary systems" Lab Chip, 7, 119-125, 2007.*
Lai, Edwina S; et al; "Designing a tubular matrix of oriented collagen fibrils for tissue engineering" Acta Biomaterialia, 7, 2448-2456, 2011.*
Breitenbach, Jorg; "Melt extrusion: from process to drug delivery technology" European Journal of Pharmaceutics and Biopharmaceutics, 54, 107-117, 2002.*
Forgacs, Gabor; et al; "Assembly of Collagen Matrices as a Phase Transition Revealed by Structural and Rheologic Studies" Biophysical Journal, 84, 1272-1280, 2003.*
International Search Report and Written Opinion of International application No. PCT/CA2013/050615.
Translation of foreign patent document No. CN 102266589.
Supplementary European Search Report with regard to EP 13 82 8696 dated Feb. 16, 2016.
Ayres et al., "Modulation of anisotropy in electrospun tissue-engineering scaffolds: Analysis of fiber alignment by the fast Fourier transform", Biomaterials, 2006, vol. 27, pp. 5524-5534.
Ayres et al., "Measuring fiber alignment in electrospun scaffolds: a user's guide to the 2D fast Fourier transform approach", Journal of Biomaterials Science, Polymer Edition, 2008, vol. 19, No. 5, pp. 603-621.
Knight et al., "In vitro formation by reverse dialysis of collagen gels containing highly oriented arrays of fibrils", John Wiley & Sons Inc., 1998, pp. 185-191.
Besseau et al., "Production of ordered collagen matrices for three-dimensional cell culture", Biomaterials, 2002, vol. 23, pp. 27-36.

(Continued)

*Primary Examiner* — David Berke-Schlessel
(74) *Attorney, Agent, or Firm* — BCF LLP

(57) ABSTRACT

There is provided a method for preparing a dense hydrogel comprising providing an at least partially gelled hydrogel, placing the at least partially gelled hydrogel in fluid communication with an end of a capillary, and driving the at least partially gelled hydrogel into the capillary to form a dense hydrogel. There is also provided a system for preparing the dense hydrogel comprising a capillary having a bore; and a driver in communication with an end of the capillary for driving an at least partially gelled hydrogel into the bore of the capillary to form a dense hydrogel.

11 Claims, 12 Drawing Sheets

(56) References Cited

OTHER PUBLICATIONS

Brown et al., "Ultrarapid Engineering of Biomimetic Materials and Tissues: Fabrication of Nano- and Microstructures by Plastic Compression", Advanced Functional Materials, 2005, vol. 15, pp. 1762-1770.

Mosser et al., "Dense tissue-like collagen matrices formed in cell-free conditions", Matrix Biology, 2006, vol. 25, 2006, pp. 3-13.

Lai et al., "Designing a tubular matrix of oriented collagen fibrils for tissue engineering", Acta Biomaterialia, 2011, vol. 7, pp. 2448-2456.

Macaya et al., "Injectable Collagen—Genipin Gel for the Treatment of Spinal Cord Injury: In Vitro Studies", Advanced Functional Materials, 2011, vol. 21, pp. 4788-4797.

Zeugolis et al., "Engineering Extruded Collagen Fibers for Biomedical Applications", Journal of Applied Polymer Science, 2008, vol. 108, pp. 2886-2894.

Kureshi et al., "Alignment hierarchies: engineering architecture from the nanometre to the micrometre scale", J. Royal Society Interface, 2010, vol. 7, pp. S707-S716.

Arany et al., "At the edge of translation—materials to program cells for directed differentiation", Oral Diseases, 2011, vol. 17, pp. 241-251.

Roeder et al., "Tensile Mechanical Properties of Three-Dimensional Type I Collagen Extracellular Matrices With Varied Microstructure", J. Biomedical Engineering, 2002, vol. 124, pp. 214-222.

Guo et al., "Flow and magnetic field induced collagen alignment", Biomaterials, 2007, vol. 28, pp. 1105-1114.

Lanfer et al., "Aligned fibrillar collagen matrices obtained by shear flow deposition", Biomaterials, 2008, vol. 29, pp. 3888-3895.

Cheng et al., "An electrochemical fabrication process for the assembly of anisotropically oriented collagen bundles", Biomaterials, 2008, vol. 29, pp. 3278-3288.

Marelli et al., "Silk fibroin derived polypeptide-induced biomineralization of collagen", Biomaterials, 2012, vol. 33, pp. 102-108.

Millet et al., "Pattern analysis and spatial distribution of neurons in culture", Integrative Biology, 2011, vol. 3, pp. 1167-1178.

\* cited by examiner

DENSE HYDROGELS

CROSS-REFERENCE TO RELATED APPLICATIONS

The present application claims benefit of U.S. Provisional Application No. 61/681,209 filed Aug. 9, 2012, and of U.S. Provisional Application No. 61/788,150 filed Mar. 15, 2013, and is a National Phase Entry of PCT application No. PCT/CA2013/050615 filed Aug. 9, 2013, which are hereby incorporated herein by reference in their entirety.

FIELD

This invention relates to dense hydrogels, more specifically although not exclusively, to dense hydrogels as biomaterials.

BACKGROUND

Biomaterials are used for the repair, replacement, construction, engineering, regeneration or augmentation of hard and soft issue in response to diseases, such as degenerative diseases and other conditions; trauma, as well as cosmetic treatments, injectable biomaterials can reduce the invasiveness, time, cost and difficulty of the surgical operation and of the post-operation period. However, biomaterials which are based on hydrogels and which can be injected, such as collagen, rely on the in situ self-assembly of the biomaterial. In other words, the hydrogel undergoes gelation in vivo after delivery to the injection site. This does not allow full control over the morphological, mechanical and biological properties of the gelled biomaterial and therefore does not allow tailoring of the biomaterial properties to specific situations. For example, the three-dimensional architecture can play an important role in tissue regeneration, therefore control and predictability of this architecture is desirable. Also, the injected biomaterial can dissipate from the intended injection site.

Therefore, it is desired to overcome or reduce at least some of the above-described problems.

SUMMARY

The embodiments of the present disclosure reduce the difficulties and disadvantages of the aforesaid designs.

From one aspect, there is provided a method for preparing a dense hydrogel, the method comprising providing an at least partially gelled hydrogel; placing the at least partially gelled hydrogel in fluid communication with an end of a capillary, and driving the at least partially gelled hydrogel into the capillary to form a dense hydrogel. The driving step may comprise applying a shear stress.

In certain embodiments, the driving step also comprises compaction of the at leas partially gelled hydrogel at the same time as driving it into the capillary to form the dense hydrogel. The compaction may comprise application of a shear stress which may be achieved or enhanced by driving the at least partially gelled hydrogel into the capillary for example when the at least partially gelled has a cohesive form. This may be when the at least partially gelled hydrogel is a hydrogel in which the gelation process has reached a steady state. The compaction may be achieved or enhanced by the at least partially gelled hydrogel having a configuration with a larger diameter than a diameter of the capillary. In certain embodiments, the dense hydrogel may be in a directly deliverable form such as injectable. In the case of forming an injectable hydrogel, the hydrogel has a diameter suitable for injection due to the dimensions of the capillary in which the dense hydrogel is formed. In certain embodiments, the at least partially gelled hydrogel includes a solid phase and the resistant dense hydrogel has a substantially aligned solid phase, such as fibrils. Therefore, in certain embodiments of the present method, a dense hydrogel with aligned fibrils can be obtained by compaction into a capillary, and not necessitating the use of cells etc.

From another aspect there is provided a method for preparing a dense hydrogel, the method comprising providing a hydrogel precursor; initiating gelling of the hydrogel precursor to form an at least partially gelled hydrogel; and driving and/or compacting the at least partially gelled hydrogel into a capillary to form a dense hydrogel. The driving step may comprise applying a shear stress.

From a further aspect, there is provided a method for preparing a dense hydrogel, the method comprising providing an at least partially gelled hydrogel including a solid phase; placing the at least partially gelled hydrogel in fluid communication with an end of a capillary, and compacting the at least partially gelled hydrogel into the capillary to form a dense hydrogel with a substantially aligned solid phase. The driving step may comprise applying a shear stress.

The above aspects of the method can be performed at room temperature. The dense hydrogel can be formed from the at least partially gelled hydrogel in less than 2 hours, less than 1.5 hours, less than 1 hour, less than 30 minutes, or less than 15 minutes. This time may be longer if a culture time is required for incorporated cells, or if a longer gelling period is required. However, the time required to drive the partially gelled hydrogel into and/or through the capillary may be about 60 minutes, about 45 minutes, about 30 minutes, shout 15 minutes, or about 10 minutes. This time will depend on the starting density of the at least partially gelled hydrogel, the diameter of the capillary, the volume of the at least partially gelled hydrogel and the pressure differential applied across the at least partially gelled hydrogel.

The dense hydrogel obtained by certain embodiments of the present method is injectable into a human or animal site or deliverable through a catheter, a needle or the like. The capillary may be a needle having a bore, such as a hypodermic needle or a blunt ended needle.

In certain embodiments of the above aspects, driving or compacting the at least partially gelled hydrogel into the capillary comprises applying a pressure differential between the capillary and the least partially gelled hydrogel.

In certain embodiments of the above aspects, driving or compacting the at least partially gelled hydrogel into the capillary comprises exerting a positive pressure on the at least partially gelled hydrogel whilst the at least partially gelled hydrogel is in communication with the capillary. In other words, the positive pressure is applied on the uncompleted at least partially gelled hydrogel. By positive pressure, is meant pressure which is more than atmospheric pressure which may be present. The positive pressure can be exerted by placing the uncompacted at least partially gelled hydrogel in an environment which can be pressurized. The environment may be air or liquid within a scalable and pressurizable container or chamber. For example, the environment may be liquid. The positive pressure applied to the at least partially gelled hydrogel by the liquid may be increased by allowing gas to flow into the container in communication with the liquid. Driving or compaction of the at least partially gelled hydrogel into the capillary can be assisted or enhanced by removing liquid from the at least partially gelled hydrogel before or at the same time as driving it through the capillary. The removal of liquid may also accelerate the gelation process. In certain embodiments, this is achieved by allowing osmotic movement of the water from the at least partially gelled hydrogel to the environment. In this case, the environment may be a hypertonic liquid. A semi-permeable membrane may be provided around the at least partially gelled hydrogel to allow movement of water out of the at least partially gelled hydrogel by osmosis. The semi-permeable membrane may be made of cellulose or cellophane and include pores. Removal of the liquid is optional. In certain embodiments, the capillary may extend at least partially or fully through a wall of the scalable pressurizable container.

Alternatively, the positive pressure may be applied by using a membrane around the uncompacted at least partially gelled hydrogel, wherein the membrane is made of a material which can contract on application of an external stimulus such as a temperature change, a pH change, a chemical change. Examples of such materials include shape memory alloys or shape memory polymers such as Nitinol™ and Flexinol™.

Alternatively, the positive pressure may be applied by any another means such as using an actuator such as a plunger.

In certain embodiments, the method may further comprise exerting a negative pressure on the at least partially gelled hydrogel through the capillary. The negative pressure may be applied through the first end of the capillary. In this case, the negative pressure will be exerted on the formed dense hydrogel in the capillary. The negative pressure may be applied by a driver connectable to, or in communication with, the second end of the capillary. The driver may be a manual or automatic pump, or an actuator such as a piston and cylinder of a syringe. Driving or compaction of the at least partially gelled hydrogel into the capillary can be assisted or enhanced by removing liquid from the at least partially gelled hydrogel before or at the same time as driving it into the capillary. The removal of liquid may also accelerate the gelation process. In certain embodiments, this is achieved by capillary action, which may be performed before, or at the same time as, driving the at least partially gelled hydrogel into the capillary. An absorbent material may be used such as blotting paper, filter paper, sponge-like materials, or any other means of removing a liquid component from a hydrogel. Removal of the liquid is optional.

In certain embodiments, both a negative pressure and a positive pressure are applied, for example a negative pressure on the dense hydrogel at least partially gelled hydrogel, and a positive pressure on the uncompacted at least partially gelled hydrogel.

Certain embodiments of the method further comprise providing a hydrogel precursor and initiating gelling of the hydrogel precursor to form the at least partially gelled hydrogel. The step of initiating gelling of the hydrogel precursor may include incubation of the hydrogel precursor in a support means such as a cast, mould or tray. By incubating is meant allowing the hydrogel precursor to self-assemble with or without the use of external stimuli such as heating, cooling, pH changes, cross-linkers etc. In certain embodiments, the hydrogel precursor is a collagen hydrogel precursor, such as type I collagen solution. Gelling of the collagen hydrogel precursor can be initiated and controlled using temperature. The hydrogel precursor can be exposed to a temperature of between about 6° C. to about 40° C. The skilled person will realize that the duration of time that the hydrogel precursor takes to gel ('self-assemble') may depend on the applied temperature. For example, a shorter time may be required at a higher temperature. In certain embodiments, the collagen hydrogel precursor is incubated for at least about 15 minutes at a temperature of about 37° C., more preferably for about at least 10 minutes at a temperature of about 37° C., and most preferably for about 15 minutes at a temperature of about 37° C. In another embodiment, the collagen hydrogel precursor is incubated for at least about 10 minutes, or about 15 minutes, or about 20 minutes, or about 25 minutes at room temperature (about 22° C.). Gelling can also be initiated at other temperatures and for other durations of time. In certain embodiments, gelling can be initiated in a refrigerator at about 6° C. for at least about 30 minutes.

In certain embodiments, the driving step may be repeated through capillaries of smaller sizes. For example, the at least partially gelled hydrogel may be first driven into a first capillary, followed by a second capillary, in which the second capillary has a smaller diameter than the first capillary. This approach can avoid or minimize clumping or loss of gel functionality. The first and second capillaries may be connectable or separate. The first and second capillaries may be one piece with a graduated diameter e.g. cone shaped.

Advantageously, it has been found by the present inventors that driving the at least partially gelled hydrogel into the capillary, substantially aligns the solid phase. In the case of collagen, substantially aligned nano-fibrils are obtained and this alignment is retained in the dense hydrogel.

Preferably, the hydrogel is a biomaterial with possible uses as a tissue equivalent or an in vivo delivery system. In certain embodiments, the hydrogel is selected from naturally derived materials, synthetically derived materials and combinations of the same, for example: collagen, hyaluronan, chitosan, fibrin, gelatin, alginate, agarose, chondroitin sulphate, polyacrylamide, polyethylene glycol (PEG), poly vinyl alcohol (PVA), polyacrylic acid (PAA), hydroxy ethyl methacrylate (HEMA), polyanhydrides, poly(propylene fumarate) (PPF) and the like.

In certain embodiments, the dense hydrogel is based on collagenous materials and is inherently biocompatible. The hydrogel is porous enough to allow cell seeding and penetration, as well as oxygen and nutrient transport to the seeded cells. In vivo, the hydrogel can be reabsorbed in a period of time compatible with the tissue repair process. It mimics the extracellular structure of tissues due to its collagenous material base. The biomaterial is non-immunogenic.

In certain embodiment, the method further comprises adding at least one bioactive agent to the at least partially gelled hydrogel. This may be performed before or during gelling of the at least partially gelled hydrogel. In certain embodiments, the bioactive agents can be added to the hydrogel precursor or to the at least partially gelled hydrogel before passing the hydrogel into the capillary. The bioactive agents may be selected from cells, genes, drug molecules, therapeutic agents, particles, osteogenic agents osteoconductive agents, osteoinductive agents, anti-inflammatory agents, growth factors, and the like. These bioactive agents can be added to the hydrogel precursor before gelation begins, or during gelation. In certain embodiments, as the method is performed at room temperature or under physiologic conditions, cell viability may be maintained. No adverse effect of gelling on the ended bioactive agents has been observed or is expected.

Examples of particles include bioactive glass, soluble glass, resorbable calcium phosphate, hydroxyapatite, calcium carbonate, calcium sulphate, glass-ceramics, to name a few. The particles may be microspheres. They may be porous or non-porous. The cells may include those involved in hard and soft tissue generation, regeneration, repair and maintenance, for example mesenchymal stem cells, bone marrow stem cell, osteoblasts, preosteoblasts, fibroblasts, muscle cells and chondrocytes, and the like. Therapeutic agents can include hormones, bone morphogenic proteins, antimicrobials, anti-rejection agents and the like. The drugs can be any molecules for disease, condition or symptom treatment or control, anti-inflammatory, growth factors, peptides, antibodies, vesicle for release of ions, release of gas, release of nutrients, enzymes, as well as nano carriers within the dense hydrogels. In this way, the biomaterial may be used as a substance carrier or as a delivery vehicle, such as for controlled release of drugs or therapeutic agents. It is thought that sustained release may improve the success of the therapy and minimize the possible side effects. This is particularly true in the case of cancer treatment, where antineoplastic drugs are very debilitating for the patient body. Delivering the drugs, for sustained release, in an injectable biomaterial, is therefore advantageous.

The particles can be fibroin-derived polypeptides, preferably polypeptides which have been chymotryptically isolated and extracted from silk fibroin such as a soluble fraction Cs, a precipitated fraction Cp, or a combination of the Cs and Cp fractions (as described in PCT/CA2012/000192, the contents of which are herein incorporated by reference).

The cells can be any type of cells, such as mammalian cells for example stem cells (embryonic or mesenchymal), nerve cells, osteoblasts, smooth muscle cells, myoblasts, fibroblasts, populations of cells such as from a bone marrow aspirate, and the like. Combinations of cell types can also be included.

In certain embodiments, the bioactive agents align along the substantially aligned solid phase of the hydrogel. In one example, cells and other agents added to a collagen precursor align along the collagen nano-fibrils once the dense hydrogel is formed.

In certain embodiments, different types of bioactive agent may be placed in different zones of the at least partially gelled hydrogel. The at least partially gelled hydrogel may comprise layers of different gels.

In certain embodiments, the method further comprises ejecting the dense hydrogel from the capillary. The negative or positive pressure driver can be used. In certain embodiments, the method further comprises ejecting the dense hydrogel into a chamber from the capillary. The chamber can be a syringe chamber. In this case, the capillary can be an end of the syringe or a needle attached to the syringe. The chamber can also be any other type of storage chamber. The chamber may include a storage media such as saline or phosphate buffered solution. In this way, the formed dense hydrogel can be stored until required for delivery to a patient.

In certain embodiments, the method further comprises cutting or shaping the dense hydrogel, for example into particulate form. A particulate form dense hydrogel will have a higher surface area to volume ratio which may have an enhanced therapeutic effect. These dense hydrogel particulates may then be suspended in liquid before delivering to a treatment site.

In certain embodiments, the dense hydrogel may be elected into a delivery device from the capillary or from the chamber. The delivery device may be a needle, a catheter or the like.

Certain embodiments of the method may further include sterilization methods to sterilize the dense hydrogel before delivery into a patient. The sterilization may also occur before the dense hydrogel is formed, especially if the capillary is a needle. In certain embodiments of the method, the at least partially gelled hydrogel can preserve its sterility as the dense hydrogel need not be handled up until and including delivery into a patient.

In certain embodiments where the resultant dense hydrogel is injectable, the method may further comprise delivering the dense hydrogel to a site in a human or animal patient. A delivery device, attachable to the capillary or the storage means, may be used. The delivery device may be a needle or a catheter. The dense hydrogel may also be delivered directly from the capillary without storing.

In certain embodiments, by using readily available needles as the capillary or delivery device, syringes as the driver and/or catheters as the delivery device, this method provides a cost effective way of producing a dense hydrogel which is injectable. Also, it can eliminate the need for further processing or manipulating the dense hydrogel. Sterility can be maintained. By forming the dense hydrogel with aligned fibers in a needle or a syringe or another delivery vehicle, the dense hydrogel may be delivered to a patient without requiring any additional steps or handling. No additional shaping or cutting is required. In certain embodiments, the capillary has an internal diameter of about 0.1 to about 10 mm, about 0.1 to about 5 mm, about 0.1 to about 4 mm, about 0.1 to about 3 mm, about 0.1 to about 2 mm, about 0.1 to about 1 mm. For other applications of the present disclosure, the internal diameter of the capillary may be much wider, for example in applications of implantable biomaterials. The internal diameter of the capillary may be selected according to the density required in the dense hydrogel as the inventors have discovered that reducing the capillary internal diameter increases the collagen fibrillar density or solid weight percent.

From another aspect, there is provided a dense hydrogel made using the method described above. The dense hydrogel may have a substantially aligned solid phase, and the density of the solid phase may be from about 2 to about 60 wt %.

From a yet further aspect, there is provided a dense hydrogel with a substantially aligned solid phase, wherein the density of the solid phase is from about 2 to about 60 wt %.

In certain embodiments of the above aspects of the dense hydrogel, the density of the solid phase can be from about 2 to about 55%, about 5 to about 50%, about 5 to about 45%, about 10 to about 40%, about 15 to about 35%, about 20 to about 30%, about 5 to about 60%, about 10 to about 60%, about 15 to about 60%, about 20 to about 60%, about 25 to about 60%, about 30 to about 60%, about 35 to about 60%, about 40 to about 60%, about 45 to about 60%, or about 50 to about 60%.

In certain embodiments of the above aspects, the solid phase of the hydrogel is fibrillar and the alignment of the fibers is >0.038 unit when measured using the method reported by Ayres et al. [Ayres et al., Biomaterials, 2006, 27(32): 5524-5534; and Ayres et al., J. Biomater. Sci. Polymer Edn, Vol. 19, No. 5, pp. 603-621 (2008)], the contents of which are incorporated herein by reference. Briefly, this method of measuring fibre alignment comprises using fast Fourier transform (FFT) to convert an image of the fibrils to an output image comprising grayscale pixels that are distributed in a pattern that reflects the degree of fibre alignment in the original image. A graphical depiction can then be generated by placing a circular projection on the output image and conducting a radial summation of the pixel intensities for each degree between 0-360° in 1° increments.

The summed pixel intensities at each degree were then plotted as a function of degree. The higher the peak, the more aligned the fibrils. Using this method, 0 indicates isotropy and 0.15 indicates anisotropy. For a nanofibrous isotropic material, due to presence of pores and voids, the typical score is 0.016 unit, while anisotropic properties correspond to a score>0.035 units.

In certain embodiments, the dense hydrogel has a configuration suitable for injection into a treatment site of a patient. Configuration comprises at least one of shape and size (dimensions). The dense hydrogel is dimensioned and shaped in order to be deliverable through a needle or a catheter. The dense hydrogel can have a substantially cylindrical shape having a diameter corresponding to or less than a diameter of a needle or a catheter. The dense hydrogel may be a cohesive biomaterial. The dense hydrogel may also be in particulate form, for example, for delivery as a suspension through a needle or a catheter.

In certain embodiments, the hydrogel is selected from naturally derived materials, synthetically derived materials and combinations of the same, for example: collagen, hyaluronan, chitosan, fibrin, gelatin, alginate, agarose, chondroitin sulphate, polyacrylamide, polyethylene glycol (PEG), poly vinyl alcohol (PVA), polyacrylic acid (PAA), hydroxy ethyl methacrylate (HEMA), polyanhydrides, poly (propylene fumarate) (PPF) and the like.

In certain embodiments, the hydrogel further includes at least one of cells, genes, drug molecules, therapeutic agents, particles, bioactive agents, osteogenic agents, osteoconductive agents, osteoinductive agents, anti-inflammatory agents, growth factors, fibroin derived polypeptide particles, and combinations of the same. These cells, molecules, agents, particles etc. can also be aligned with the aligned fibrils.

In certain embodiments, the particles are fibroin-derived polypeptides, such as polypeptides isolated and extracted from silk fibroin such as a soluble fraction Cs, a precipitated fraction Cp, or a combination of the Cs and Cp fractions. In certain embodiments, the cells can be any type of cells, such as mammalian cells for example stem cells (embryonic or mesenchymal), nerve cells, osteoblasts, smooth muscle cells, myoblasts, fibroblasts, populations of cells such as from a bone marrow aspirate, and the like. Combinations of cell types can also be included. In certain embodiments, the cells are aligned along the solid phase.

In certain embodiments, different types of bioactive agent may be placed in different zones of the at least partially gelled hydrogel. The at least partially gelled hydrogel may comprise layers of different gels.

From a yet further aspect, there is provided a system for preparing a dense hydrogel, the system comprising a capillary having a bore; and a driver which can be in fluid communication with as least a first end of the capillary for driving an at least partially gelled hydrogel into the bore of the capillary to form a dense hydrogel.

In certain embodiments of the system, the driver can apply a pressure differential between the capillary and site least partially gelled hydrogel. In certain embodiments, the driver can also cause the at least partially gelled hydrogel to compress at the same time as driving it into and/or through the capillary to form the dense hydrogel.

In certain embodiments, the driver can exert a positive pressure on the at least partially gelled hydrogel, for example whilst the at least partially gelled hydrogel is in communication with the capillary. In these embodiments, the driver can be a sealable chamber for receiving the at least partially gelled hydrogel and comprising an environment which can apply pressure on the at least partially gelled hydrogel. The environment, may be air or liquid. For example, the environment may be liquid. The positive pressure applied to the at least partially gelled hydrogel by the liquid may be increased by allowing gas to flow into the container through an inlet in order to pressurize the liquid.

In certain embodiments, the system further comprises a membrane separating the at least partially gelled hydrogel from the environment. The system may be a semi-permeable membrane for allowing liquid to leave the at least partially gelled hydrogel by osmosis. In this case, the environment may be a hypertonic liquid. The semi-permeable membrane may be made of cellulose or cellophane and include pores. Removal of the liquid is optional. In certain embodiments, the capillary may extend at least partially or fully through a wall of the sealable pressurizable container.

Alternatively, the positive pressure driver may be a membrane or sleeve for receiving the at least partially gelled hydrogel, wherein the membrane is made of a material which can contract on application of an external stimulus, such as a temperature change, a pH change, a chemical change. Examples of such materials include shape memory alloys or shape memory polymers such as Nitinol™ and Flexinol™.

Alternatively, any other means for applying a positive pressure on the at least partially gelled hydrogel may be used, such as an actuator (e.g. in a syringe).

In certain embodiments, the driver can exert a negative pressure on the at least partially gelled hydrogel, or on the dense hydrogel in the capillary. The driver may be attachable to a second end of the capillary in order to apply the negative pressure across the capillary. The driver may be a manual or automatic pump, or an actuator such as a piston and cylinder of a syringe. In certain embodiments, the driver is an actuator and movement of the actuator away from the second end of the capillary can exert negative pressure through the capillary. The actuator may be manually or automatically manipulatable. The system may further compose a valve in between the negative pressure driver and the capillary second end for equalizing pressure between the capillary and the driver.

The system may further comprise a removal means in communication with the at least partially gelled hydrogel for removing liquid from the at least partially gelled hydrogel. In certain embodiments, this is achieved by capillary action, which may be performed before, or at the same time as, driving the at least partially gelled hydrogel into the capillary. The removal means may comprise an absorbent material such as blotting paper, filter paper, sponge-like materials, or any other means of removing a liquid component from a hydrogel. Removal of the liquid is optional.

In certain embodiments, the system comprises more than one driver, for example one for applying a negative pressure on the dense hydrogel (e.g. the pump and/or the syringe attachable to the capillary second end), and the other for applying a positive pressure on the uncompacted hydrogel (e.g. the scalable and pressurizable chamber for communicating with the at least partially gelled hydrogel.

In certain embodiments, the system further comprises a hydrogel precursor and/or the at least partially gelled hydrogel. The hydrogel precursor and/or the at least partially gelled hydrogel may be a biocompatible material and/or a biomaterial. The biocompatible material may be selected from collagen (e.g. collagen type I), hyaluronan, chitosan, fibrin, gelatin, alginate, agarose, poly(ethylene glycol) (PEG), poly(vinyl alcohol) (PVA), polyacrylic acid (PAA), hydroxy ethyl methacrylate (HEMA), polyanhydrides, polypropylene fumarate) (PPF) and polyacrylates, or mixtures of the same.

The hydrogel precursor and/or the at least partially gelled hydrogel may include at least one bioactive agent selected from cells (such as stem cells, fibroblasts etc.), genes, drug molecules, therapeutic agents, particles, osteogenic agents, osteoinductive agents, osteoinductive agents, anti-inflammatory agents and growth factors. The particles may be fibroin-derived polypeptides which are a soluble fraction Cs, a precipitated fraction Cp, or a combination of the Cs and Cp fractions, which have been isolated and extracted from silk fibroin. Examples of particles include bioactive glass, soluble glass, resorbable calcium phosphate, hydroxyapatite, calcium carbonate, calcium sulphate, glass-ceramics, to name a few. The particles may be microspheres. They may be porous or non-porous. The cells may include those involved in hard and soft tissue generation, regeneration, repair and maintenance, for example mesenchymal stem cells, bone marrow stem cell osteoblasts, preosteoblasts, fibroblasts, muscle cells and chondrocytes, and the like. Therapeutic agents can include hormones, bone morphogenic proteins, antimicrobials, anti-rejection agents and the like. The drugs can be any molecules for disease, condition or symptom treatment or control, anti-inflammatory, growth factors, peptides, antibodies, vesicle for release of ions, release of gas, release of nutrients, enzymes, as well as nano carriers within the dense hydrogels. In this way, the biomaterial may be used as a substance carrier or as a delivery vehicle, such as for controlled release of drugs or therapeutic agents.

In certain embodiments, the at least partially gelled hydrogel may be a hydrogel in which the gelation process has reached a steady state. The at least partially gelled hydrogel may be in a cohesive form.

The system may further comprise a support means for supporting the at least partially gelled hydrogel and/or a hydrogel precursor. The support means may be a mould, a case or a tray. In the case of the hydrogel precursor, gelation may occur in the support means. Accordingly, the system may further comprise devices or reagents for initiating, stimulating or allowing gelation to occur, such as a heating device, a cooling device, a pH adjuster, cross-linkers, etc.

In certain embodiments, the dense hydrogel formed in the capillary is a tissue equivalent material having a substantially aligned solid phase. In certain embodiments, the dense hydrogel may be in a directly deliverable form such as injectable.

In certain embodiments, the capillary has a diameter suitable for forming an injectable dense hydrogel. For example, the capillary has an internal diameter of about 0.1 to about 10 mm, about 0.1 to about 5 mm, about 0.1 to about 4 mm, about 0.1 to about 3 mm, about 0.1 to about 2 mm, or about 0.1 to about 1 mm. For non-injectable applications of the dense hydrogel, the internal diameter of the capillary may be much wider, for example in applications of implantable biomaterials. The internal diameter of the capillary may be selected according to the amount of the solid phase required in the dense hydrogel. The diameter of the at least partially gelled hydrogel may be larger than that of the capillary. The capillary can be a needle with a bore, such as a hyperdermic needle or a blunt-ended needle. The needle can have different gauges (bore diameters).

In certain embodiments, at least two capillaries with different internal dimensions may be provided. For example, the system may comprise a first capillary and a second capillary through which the at least partially gelled hydrogel is driven, in which the second capillary has a smaller diameter than the first capillary. This approach can avoid or minimize clumping or loss of gel functionality. The first and second capillaries may be connectable or separate. The first and second capillaries may be one piece with a graduated diameter e.g. cone shaped.

In certain embodiments, the system further comprises a chamber removably attachable to the capillary for receiving the dense hydrogel from the capillary. The chamber can be a syringe chamber. In this case, the capillary can be an end of the syringe or a needle attached to the syringe. The chamber can also be any other type of storage chamber. The chamber may include a storage media such as saline or phosphate buffered solution. In this way, the formed dense hydrogel can be stored until required for delivery to a patient.

The system may also comprise a delivery device for delivering the dense hydrogel to a treatment site from the capillary or from the chamber. The delivery device may be a needle, a catheter or the like.

The negative or positive pressure driver may be used to push the dense hydrogel out of the capillary and into the chamber or the delivery device.

Advantageously, in certain embodiments, when the capillary is a needle and the chamber is a syringe attachable to the needle, a variety of different size combinations (needle internal bore/syringe volume) may be used. Also, as needles and syringes are commonly available and cheap, this provides a cost effective way of producing a dense hydrogel which is injectable. Once the dense hydrogel is formed and stored in the syringe, a needle with a smaller bore, or appropriate end, or catheter may be attached to the syringe for delivery of the dense hydrogel.

From a yet further aspect, there is provided a kit for forming a dense hydrogel including one or more components of the abovedescribed system, such as the capillary and at least one driver. Therefore, there is provided a kit for forming a dense hydrogel, the kit comprising a capillary having a bore, and a driver attachable to a first end of the capillary for driving an at least partially gelled hydrogel into the bore of the capillary to form a dense hydrogel.

In certain embodiments, the kit may further comprise at least one of a hydrogel precursor or an at least partially gelled hydrogel. For example, the hydrogel precursor may be a collagen hydrogel precursor, such as type I collagen solution.

In certain embodiments, the capillary is a needle with a bore. A number of different capillaries with different bore sizes may be provided.

In certain embodiments, the at least one driver may be a pump attachable to an end of the capillary, and/or an actuator such as a syringe with a piston attachable to an end of the capillary. Additionally or alternatively, the driver may be a sealable chamber for receiving the at least partially gelled hydrogel and having an environment which can pressurize the at least partially gelled hydrogel and/or a shape memory alloy/polymer membrane.

In certain embodiments, the kit may include a support means for supporting a hydrogel precursor or an at least partially gelled hydrogel.

In certain embodiments, the kit can further comprise a removal means for removing water from the at least partially hydrogel. The removal means can be an absorbent material or an osmotic water removal system, for example comprising a semi-permeable membrane and a hypertonic medium.

In certain embodiments, the kit further comprises materials required to make the hydrogel, such as monomers, bioactive agents, or solutions to allow self-assembly. Different reagents such as cross linkers may be included to form or to tailor the properties of the gel. In addition, several consumables (e.g. macromolecules, bioactive molecules, cells, genes, peptides, proteins, metal particles) may also be included.

From another aspect, there is provided use of a dense hydrogel such as a dense collagen gel with aligned fibrils, as described above, as a medical device or injectable implant, or included in a medical device or implant. Advantageously, the hydrogel may be tissue equivalent implants. The dense hydrogel can be used for constructing, repairing, replacing, regenerating or augmenting soft or hard tissue; as an in vitro or in vivo construct; as a coating material; or as a delivery vehicle such as cells, genes, molecules or particles.

Other uses include regenerative medicine such as delivery of stem cells in cardiomyosplasty, wound healing, diabetes and neurodegenerative diseases, to name a few. Hard tissue can include bone and teeth. Soft tissue can include skin, muscles, tendons, ligaments, nerves, cartilage, cornea, periodontal tissue, vessels, bladder, and airway tissues such as lung, and the like. Other uses of the present dense hydrogel include in vitro or in vivo constructs; coating materials, two- or three-dimensional cell culturing substrates; cosmetic purposes such as anti-ageing treatments, face reconstruction, lip, breast and other tissue augmentation (such as an injectable filler). One medical application is cancer treatment where the dense hydrogel incorporating cancer drugs can be injected directly at the cancer site in order to obtain a sustained release of the cancer drugs. Repair of sphincters is another application.

From yet another aspect, there is provided use of a dense hydrogel such as a dense collagen gel with aligned fibrils, as described above, as a delivery vehicle for cells, genes, drug molecules, therapeutic agents, particles, bioactive agents, osteogenic agents osteoconductive agents, osteoinductive agents, anti-inflammatory agents, growth factors, fibroin derived polypeptide particles or the like.

From another aspect, there is provided a device for preparing a dense hydrogel, the device comprising: a chamber for receiving an at least partially gelled hydrogel or a hydrogel precursor; a first connector for connecting to a capillary into which the at least partially gelled hydrogel can be forced to form a dense hydrogel; and a second connector for connecting to a pump for applying positive pressure in the chamber. The first and second connectors can form an air-tight seal with the capillary and the pump.

From another aspect there is provided a device for preparing a dense hydrogel, the device comprising: a vessel (e.g. membrane) for receiving an at least partially gelled hydrogel or a hydrogel precursor, wherein the vessel has flexible walls, and a first connector for connecting to a capillary into which the at least partially gelled hydrogel can be forced to form a dense hydrogel; a chamber for receiving the vessel and for applying pressure to the flexible walls, in use, to force the at least partially gelled hydrogel into the capillary. The chamber can comprise an inlet for air or liquid to go into or out of the chamber. In certain embodiments, the flexible walls of the vessel comprise an osmotic membrane, and the chamber comprises a hypersonic medium in contact with the osmotic membrane for removing water from the at least partially gelled hydrogel by osmosis.

In certain embodiments of the above device aspects, the device may further comprise the pump which can be a vacuum pump for example. The device may further comprise a heat and/or humidity controller for controlling the heat and/or humidity inside the chamber. The controller can comprise a heat exchange system. The device may further comprise the capillary, the capillary having a smaller diameter than a diameter of the chamber or the vessel.

The device may be used with embodiments of the method or the system of the present disclosure.

In certain embodiments, the device, method or system may be used to densify or compress any compressible material such as a porous material, e.g. a sponge. One use of such embodiments may be for delivery of compressible materials to a location in the body through for example key-hole surgery. The compressible material may then be allowed to decompress when in position in the body.

By means of certain aspects and embodiments of the present disclosure, an injectable three dimensional dense hydrogel can be obtained. A hydrogel which is injectable has at least the following possible advantages over implantable hydrogels: minimizes infection risk, less invasive, leaves a smaller scar (if any), causes less pain to the patient, and requires shorter treatment and recovery times for the patient. Additionally, the injectable hydrogel can be delivered to awkward to reach treatment sites, allow intimate contact between the hydrogel and the host tissue, and can also carry cells, genes, drugs and other agents.

Dense hydrogels, such as dense collagen hydrogels (collagen fibrillar density higher than 5 wt %), generally have better mechanical properties than those containing a higher water content and lower fibrillar density as they more closely mimic the properties of the extracellular matrix (ECM), and may be able to support viable cells depending on the densification process. Previously reported methods of achieving dense collagen gels, for example, include reverse dialysis (Knight et al. J. Biomed. Mat. Res. 1998; 41:185-91), evaporation (Besseau et al. Biomaterials, 2002; 23:27-36), plastic compression (Brown et al. Adv. Functional Material. 2005; 15:1762-70), and continuous injection (Mosser et al. Matrix Biology, 2006; 25:3-13).

Although the use of dense hydrogels for cell delivery and regenerative medicine is appealing, to the best of the inventors' knowledge, methods described in the literature do not provide a dense hydrogel which can be injected. Dense collagen gels, for example, are in fact considered implantable and not injectable. The present system for forming a dense injectable gel, prior to its delivery in situ, has never been proposed before to the inventors' knowledge. Generally, in known systems, gels are injected in the form of solutions and then allowed to self-assemble (gel) after delivery, not before it. This does not allow for a controllable microstructure in the eventually densified hydrogel. For example, self-assembly of nanofibers is not controllable in terms of the final microstructure of the material, as monomers tend to randomly organize themselves in isotropic structures. In certain embodiments of the present disclosure, the injectable hydrogel is already dense and has a stable and controllable microstructure, before delivery to a treatment site.

This current limitation in the technology represents one of the major drawbacks for the use of dense hydrogels in clinical practice. In addition, the injection of collagen gel is limited by the weakness of the gel, which does not possesses the mechanical properties necessary to withstand the shear stress applied in the injection procedure.

The use of different cross-linkers, such as glutaraldehyde and genepin or of co-agents such as poly-ethylene glycol (PEG) and NaCl have been proposed to increase the gel mechanical properties and to allow for the extrusion of pre-formed gels through a syringe needle (Lai et al. Acta Biomaterialia, 2011; 7:2448-56; Macaya et al. Advanced Functional Materials, 2011; 21:4788-97; Zeugolis et al. J. Applied Polymer Science, 2008; 108:2886-94). However, these methods are complicated, increase the time required to form the gels, reduce cell viability and biocompatibility, may interfere with drugs and other biomacromolecules loaded into the gel and do not allow for the formation of dense collagen gels.

Certain embodiments of the present disclosure also provide a dense hydrogel with a substantially aligned solid phase. Surprisingly, using a collagen system, a fibrillar alignment was obtained by the inventors which appears to be more highly aligned than that previously seen.

This is a highly sought characteristic in the field of biomaterials, and usually requires cell-mediated rearrangement of the solid phase (e.g. fibrils) or complicated and time consuming in vitro procedures. Anisotropy is an important cue for many native tissues (e.g. nerve, tendon, ligament, bone, cornea) as it can direct cell fate and metabolism and impart unique mechanical properties to the ECM (Kureshl et al. J. Royal Society Interface, 2010; 7:S707-S16; Arany et al. Oral Diseases. 2011; 17:241-51; Roeder et al. J. Biomech. Eng. 2002; 124:214-22).

Anisotropic collagen matrices have previously been obtained through microfluidic devices or by applying strong magnetic fields to the collagen solution during self-assembly (e.g. Geo et al; Biomaterials, 2007; 28:1105-14; Lanfer et al; Biomaterials, 2008; 29:3888-95). Although successful in the micro-scale, these techniques do not provide a dense 3D biomaterial. Electric fields have also been investigated, but the high current required to achieve the alignment of the fibrils was shown to affect the structural properties of collagen causing its denaturation toward a gelatinous state (e.g. Cheng et al. Biomaterials, 2008; 29:3278-88).

A dense hydrogel according to certain embodiments of the present disclosure can be ready to inject or deliver by other means within a matter of minutes (e.g. less than about one hour, less than about 45 minutes, less than about 30 minutes, less then about 15 minutes) using readily available equipment. This may have uses as bedside applications where medical practitioners can readily make a dense hydrogel tailored for a specific application for a specific patient. The fabrication using aspects of the method, system and device of the present disclosure can be performed at room temperature. The method does not require sophisticated equipment. For example, a patient's own cells can be incorporated into the dense hydrogel. Therefore, the method can be fast and cheap which could make the method available to large numbers of patients.

Unlike known systems in the art where the gelling of a hydrogel takes place in vivo and without solid phase alignment, in certain embodiments of the present aspect of the disclosure, the hydrogel is already pre-formed before delivery to tissues with defined and predictable architecture. This architecture can be tailored to specific applications by controlling the capillary diameter, hydrogel concentration and gelling conditions.

Also, unlike prior art systems, certain embodiments of the dense hydrogel of the present disclosure (e.g. when based on collagenous materials) maintain the original biological, chemical and physical properties of the collagenous material due to its gelling or fibrillogenesis under physiologic conditions. The inventors have found that a dense collagen hydrogel made using the above-described method and system and incorporating anionic fibroin derived polypeptides (Cs) accelerated the mineralization of the dense hydrogel in simulated body fluid (SBF). It is believed that a similar effect would be achieved in vivo. The inventors also found that NIH/3T3 fibroblasts homogenously seeded in collagen gels and subjected to an embodiment of the present method resulted in viable cells aligned along a fibril direction its the resultant dense collagen. Also, mouse mesenchymal stem cells seeded in the collagen precursor at the point of fibril formation were viable in the resultant dense collagen hydrogel and were found to accelerate osteoblastic differentiation and neuronal transdifferentiation.

Definitions:

As used herein, by "biomaterial" is meant a material that is biocompatible with a human or animal body when in contact with the body such as by implantation, injection or any other contact, it can be in liquid, gel or solid form.

As used herein, by "fibroin" is meant one or more constituents of silk fibre, filament or web which can be from different animal sources such as silk worm or spider.

As used herein, by "hydrogel" is meant any dispersion of molecules, fibres or particles within a liquid (e.g. water) in which the solid (from about 0.05% to about 50% solid) is the discontinuous phase and the liquid is the continuous phase. The molecules, fibres or particles can be linked by physical and/or chemical interactions. Hydrogels can include naturally derived materials such as collagens, gelatin, alginates, hyaluranon, chitosan, fibrin, agarose, and synthetically derived materials such as chondroitin sulphate, polyacrylamide, polyethylene glycol (PEG), poly vinyl alcohol (PVA), polyacrylic acid (PAA), hydroxy ethyl methacrylate (HEMA), polyanhydrides, poly(propylene fumarate) (PPP), and the like. For example, a collagen hydrogel comprises a three-dimensional network of fibrils surrounded by interstitial fluid.

As used herein, by "hydrogel precursor" is meant any solution or suspension which can form a hydrogel through a gelling or self-assembly process. The gelling process can include fibrillogenesis and formation of a three-dimensional structure. Gelling can be initiated by applying external stimuli (e.g. control of temperature, pH, ionic strength, salt concentration, cross linking, UV light, microwave, ultrasound). For example, a collagen hydrogel precursor is a collagen solution in which the fibrils have not yet polymerized and are in soluble monomer form. The collagen solution can be an acidic tropocollagen solution, such as type I collagen extracted from rat tail. A chitosan precursor can be a hydrochloride form of chitosan.

As used herein, by "at least partially gelled hydrogel" is meant that the gelling process has begun i.e. the solid phase has started forming. It therefore includes any extent of gelling from the early to the later stages including up to the gelling process reaching a steady state. An at least partially gelled hydrogel can be identified by a measured increase in turbidity, viscosity, rigidity or cohesiveness compared so its hydrogel precursor state.

As used herein, by "capillary" is meant any small tube, channel or the like, for example a needle with a bore. Capillary need not be limited to linear shapes but may also include spherical or non-linear shapes. It will be understood that the dimensions of the capillary are sufficiently small such that driving or forcing the at least partially gelled hydrogel into the capillary will compress (compact/consolidate) the hydrogel to thereby increase its density ("dense hydrogel"). The density of the compressed hydrogel may continue to increase in the capillary or thereafter. In other words, by dense hydrogel is meant dense relative to an undensified (uncompacted) hydrogel.

As used herein, by "collagen" is meant any collagenous material dominated by collagen molecules capable of self-assembly into collagen fibrils. Includes type I and type II collagen from any source. Collagenous material may be in a liquid or gel form.

BRIEF DESCRIPTION OF THE DRAWINGS

Further aspects and advantages of the present invention will become better understood with reference to the description in association with the following in which:

FIG. 10b is a FTIR spectrum illustrating the phases of mineral formed within the collagen gel of FIG. 10a.

DETAILED DESCRIPTION OF THE INVENTION

Figure 1:
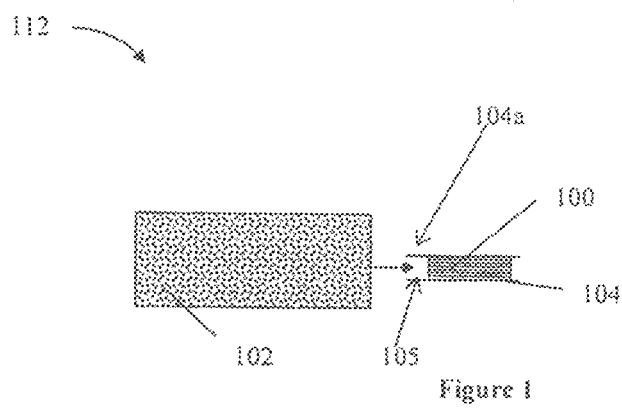
FIG. 1 is a schematic representation of a method or a system of the present disclosure for producing a dense hydrogel.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items, in the following description, the same numerical references refer to similar elements.

The examples below describe embodiments of the present invention concerning dense collagen hydrogels using collagen solutions as a hydrogel precursor. However, the invention is not limited to collagen-based systems and hydrogels other than collagen are included within the present scope, for example, gelatin, alginates, hyaluranon, chitosan, fibrin, agarose, polyacrylamide, PEG (polyethylene glycol), PAA (polyacrylic acid), HEMA (hydroxy ethyl methacrylate) and the like.

FIG. 1 illustrates a first aspect of the present disclosure directed to a method for making a dense hydrogel 100 comprising providing an at least partially gelled hydrogel 102; placing the at least partially gelled hydrogel in fluid communication with a first end 104a of a capillary 104; and driving the at least partially gelled hydrogel into the capillary 104 to form the dense hydrogel 100. In other words, the at least partially gelled hydrogel is passed through the first end 104a of the capillary. The capillary 104 has a bore 105 into which the at least partially gelled hydrogel 102 is driven. The first end 104a of the capillary may be directly or indirectly in communication with the at least partially gelled hydrogel.

FIG. 1 also illustrates a second aspect of the present disclosure directed to a system 112 for making a dense hydrogel 100 comprising the capillary 104 having the bore 105 for receiving the at least partially gelled hydrogel 102 and a driver 106 (FIGS. 2a and 2b) for driving the as least partially gelled hydrogel 102 into the capillary 104.

Figure 2A:
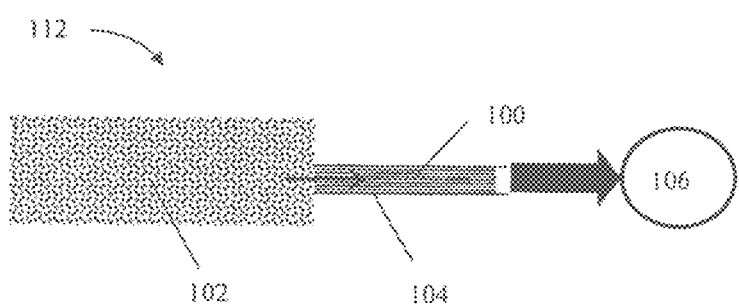
FIG. 2a illustrates certain embodiments of the method and system of FIG. 1 in which negative pressure is used.
Figure 2B:
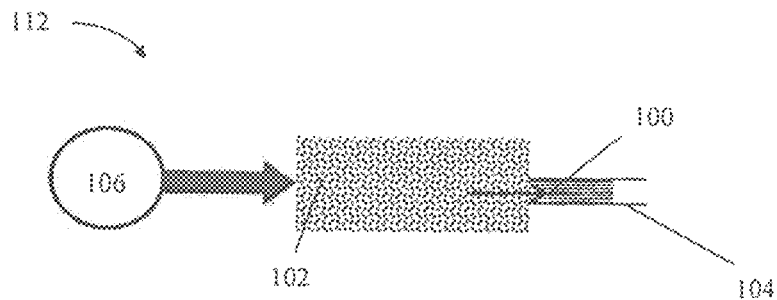
FIG. 2b illustrates certain embodiments of the method and system of FIG. 1 in which positive pressure is used.

The at least partially gelled hydrogel 102 can be driven into or through the capillary 104 by the driver 106 exerting a pressure differential between the capillary 104 and the at least partially gelled hydrogel 102. This pressure differential can be increased by applying a negative or a positive pressure on the at least partially gelled hydrogel 102 or the dense hydrogel 100. In FIG. 2a, the large arrow represents the negative pressure applied through the capillary 104 on the dense hydrogel 100. In FIG. 2b, the large arrow represents the positive pressure applied to the uncompacted hydrogel 102. Atmospheric pressure may also be present acting on the uncompacted hydrogel exposed to atmospheric pressure (especially in embodiments of FIG. 2a) but is not shown in the figures. Combinations of the same or different drivers 106 are possible for applying both negative and positive pressure.

Figure 3:
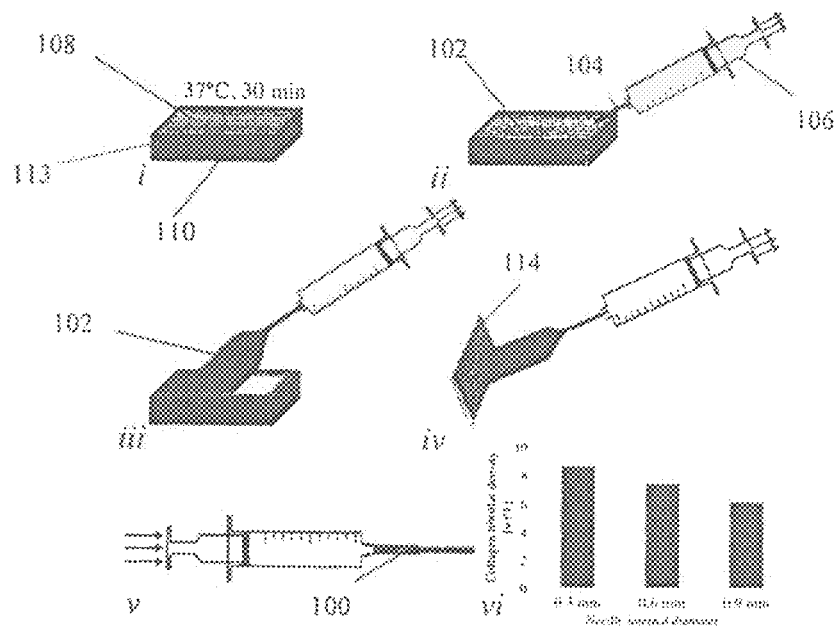
FIG. 3 illustrates certain embodiments of the method and system of FIG. 2a for producing dense hydrogels.

In one embodiment of the method and the system, which is illustrated in FIG. 3, the capillary 104 is a needle and the driver 106 is a syringe with a piston. The needle is removably attachable so the syringe. The syringe can exert a pressure differential across the capillary by actuation of the piston with the syringe cylinder. The needle can have any suitable internal bore diameter. In this embodiment, the internal bore diameter is 0.1 to about 1.5 mm, about 0.9 or about 1.2 mm (16 Gauge). In other embodiments, the internal bore diameter is about 0.1 to about 10 mm. The syringe can have any volume, for example 50 ml. In this embodiment, the at least partially gelled hydrogel 102 is driven into the needle and optionally into the syringe by exerting negative pressure on the hydrogel 102 through the needle by pulling a piston of the syringe away from the needle. In this embodiment, positive pressure is exerted by atmospheric pressure on the at least partially gelled hydrogel 102.

In the embodiment of FIG. 3, in step i, a hydrogel precursor 108, which is neutralized collagen type I solution, is provided and then at least partially gelled. The hydrogel precursor 108 is prepared by neutralizing 3.2 ml of rat tail tendon type I collagen (2.11 mg/ml. In 0.6% acetic acid) with 0.8 ml of 10 times concentrated Dulbecco Modified Eagle Medium (10×DMEM) and 37 μm of 5M NaOH. It will be appreciated that other hydrogel precursors can be used and prepared in manners known in the art. The gelling of this hydrogel precursor 108 is then be initiated by incubating the hydrogel precursor 108 in a support means 110 such as a cast (e.g. a mould of 20×40×10 mm). Incubation comprises allowing the neutralized collagen solution 108 to at least partially gel (self-assemble) in the cast 110 at a temperature of about 37° C. for at least about 10 minutes. Using this method, an at least partially gelled hydrogel 102 having a collagen fibrillar density of about 0.2 wt % can be achieved. It will be appreciated that the method can be adapted to obtain lower or higher collagen fibrillar densities for example by adjusting the initial collagen concentration and the gelation conditions (e.g. temperature, time, pH). It will also be appreciated that gelling of the collagen solution can be initiated in other ways and for different periods of time than that specified. Also other dimensions and shapes of moulds are possible.

Once the gel is at least partially formed, in step ii, the needle 104 is placed in contact with the at least partially formed gel 102 and the at least partially gelled hydrogel 102 is driven into the bore of the needle by pulling the syringe piston away from the needle which applied negative pressure across the needle bore. In step iii, the at least partially gelled get 102 continues to be driven into the needle bore by continuing to pull the syringe piston away from the needle to form a dense collagen gel 100 in the bore of the needle. The dense gel 100 may also be at least partially received into the syringe barrel.

Other drivers 106 for driving the collagen gel 102 into the capillary 104 are also possible, such as a pump, which may replace the syringe or be connected to the syringe piston for actuating the same. The process of driving the gel 102 through the capillary 104 results in a densification or compaction of the same. The total water content is lower, and the total solid phase content is higher in the dense gel 100 compared to the at least partially gelled hydrogel 102. In other words, the partially gelled hydrogel undergoes compaction whilst being driven into the capillary. It has also been found that the structure of the gel re-arranges (e.g. fibrils align) so that a dense collagen gel with aligned fibrils is obtained. In the embodiment illustrated in FIG. 3, the dense collagen gel formed using the method described above has a collagen fibrillar density of about 5.5-9.2 weight % (wt %). This collagen fibrillar density can be tailored by using different capillary internal diameters, different gelation conditions, different starting collagen concentrations, and compacting using different pressure differentials across the capillary. FIG. 3 vi illustrates how decreasing the capillary diameter in certain embodiments can increase the collagen fibrillar density in the resultant dense hydrogel.

The method of FIG. 3 optionally further comprises the step of removing liquid (such as water) from the at least partially gelled hydrogel 102 before, or at the same time as, driving it through the capillary 104 (step iv in FIG. 3). Accordingly, the system 112 illustrated in FIG. 3, includes a removal means 114 (e.g. absorbent paper such as filter paper or blotting paper) for removing liquid from the at least partially gelled hydrogel by contacting a surface of the at least partially gelled hydrogel with the absorbent paper 114 which removes water by capillary action. Negative pressure across the capillary 104 can be maintained to allow the gel to be lifted from the mould and the absorbent paper 114 to be placed on the opposite side of the gel to facilitate or accelerate fluid expulsion from the hydrated collagen gel. Removing the water can accelerate the gelling process and is an optional step. It may be necessary to release the pressure for some seconds (e.g. 1-30 seconds) in order to let the gel stabilize and then re-apply the pressure again. Alternatively, a valve can be provided for pressure equalization.

The method further comprises ejecting the dense hydrogel 100 from the capillary 104 (step v in FIG. 3). The dense hydrogel 100 can then be delivered directly to a site in a human or animal patient, or into a container for storage (not shown), using a delivery device. In the embodiment illustrated in FIG. 3, the delivery device is the same needle 104 used so form the dense hydrogel 100.

In FIG. 3, the dense collagen gel 100 is ejected from the needle 104 by applying a positive force on the dense collagen e.g. by pushing the syringe piston towards the needle. The piston can be moved manually (by hand) or automatically (by pump). The same syringe, or a different syringe containing an inert liquid medium (not shown) may be used. Of course, other ways of delivering the dense collagen from the needle are also possible, such as through the use of a pump.

Alternatively, the dense hydrogel may be passed into the syringe, and then a delivery device with a different diameter used to deliver the dense hydrogel.

The dense hydrogel may also be stored in a receiver such as the chamber/cylinder of the same or different syringe or the capillary bore until needed.

Figure 4:
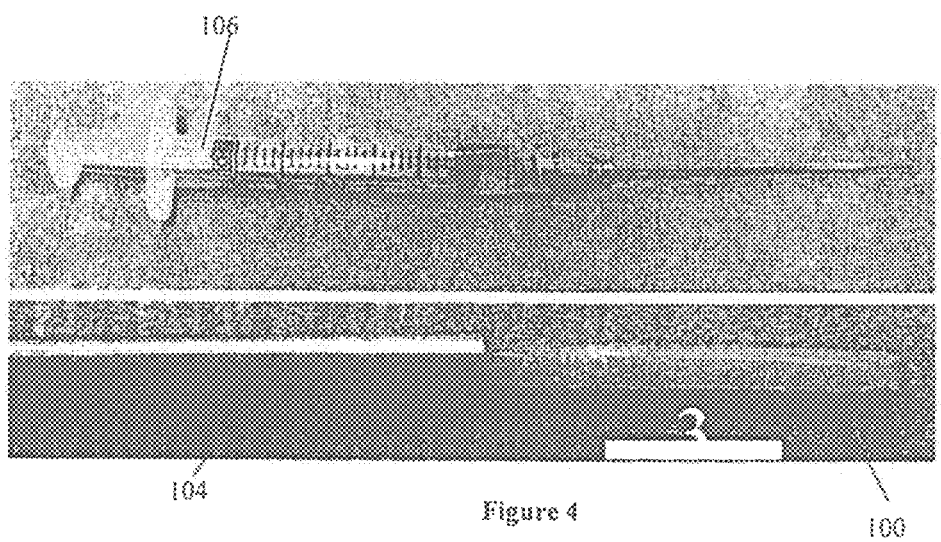
FIG. 4 illustrates a dense collagen hydrogel made according to the embodiments of FIG. 3.

In the embodiment of FIG. 3, the resultant dense collagen 100 has a size and shape corresponding to the internal size and shape of the capillary. By means of the state and shape of capillary, the resultant dense hydrogel is sized and shape to be suitable for delivery to a treatment site by injection. As can be seen in FIG. 4, the dense hydrogel 100 obtained through the method and system of FIG. 3 has a cohesive form and has a shape and size suitable for being injected.

Certain other embodiments of the method include the addition of substances into the hydrogel precursor 108, for example bioactive agents such as cells (e.g. stem cells), genes, drug molecules, therapeutic agents, particles (e.g. silk fibroin derived polypeptide particles), osteogenic agents osteoconductive agents, osteoinductive agents, anti-inflammatory agents, growth factors, enzymes (e.g. alkaline phosphatase) or the like. These can be added to the partially gelled hydrogel, during or before gelation.

Figure 5:
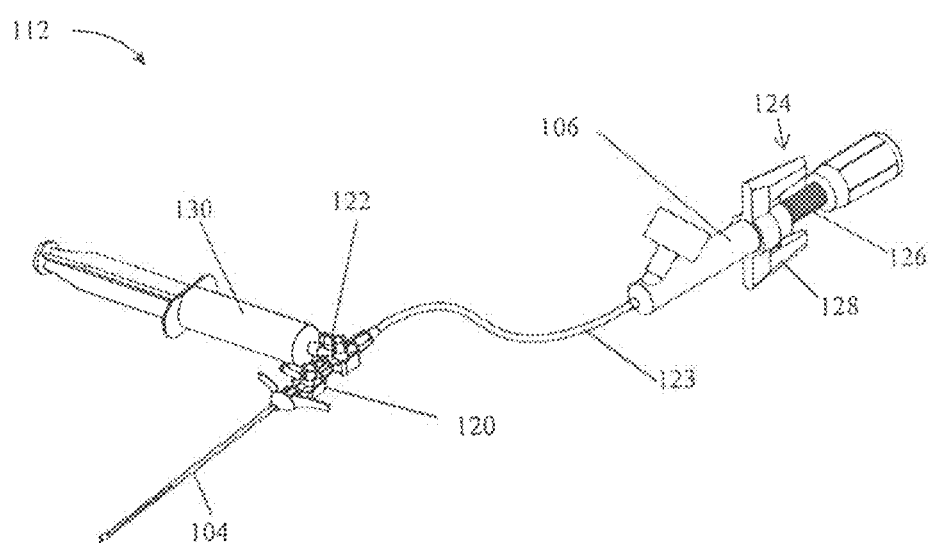
FIG. 5 illustrates further embodiments of the method and system of FIG. 2a for producing dense hydrogels.

An alternative embodiment of the method and system of FIGS. 3 and 4 is illustrated in FIG. 5. In this embodiment, the driver 106 is a pump which exerts negative pressure on the at least partially gelled hydrogel 102 or the hydrogel 100 in order to drive the at least partially formed hydrogel 102 into the capillary 104 to form the dense hydrogel 100. The dense hydrogel 100 is then delivered from the capillary bore by exerting a positive pressure on the dense gel 100 using the same or a different driver for controlled ejection of the dense hydrogel 100.

Specifically, in the system 112 of FIG. 5, the capillary 104 is a needle connectable to a first valve 120 (e.g. a three-way Luer lock valve) which in turn is connectable to a second valve 122. The second valve is then connectable to the driver 106. By means of the first and second valves 120, 122, a pathway 123 between the pump 106 and the second valve 122 can be opened and closed. The driver 106 is a pump which can preferably exert both negative and positive pressure. In this embodiment, the pump is an O-ring syringe piston with a locking mechanism 124 comprising threads 126 and a wing lock 128 (e.g. as described in U.S. Pat. No. 5,860,953, U.S. Pat. No. 5,715,542, U.S. Pat. No. 6,796,959 or U.S. Pat. No. 6,938,319). This type of pump is currently used for balloon catheterization and stent delivery procedures. The pump 106 can generate a negative or positive pressure (e.g. up to 30 ATM) in a controllable manner by engaging the threads 126 in order to maintain the selected pressure. Any other type of pump can also be used. Interchangeable needles of differing gauge sizes can be used with embodiments of the system 112 as the capillary 104. The smaller the diameter of the capillary 104, the higher the density of the dense hydrogel which can be achieved.

In use, a user selects an appropriate negative pressure to be applied from the pump 106 on the at least partially gelled hydrogel 102 which is in communication with the free end of the needle. The appropriate negative pressure can be maintained by engaging the locking mechanism 124. As the at least partially gelled hydrogel 102 is drawn into the needle bore, the dense hydrogel is formed is the needle bore. Water can be removed from the at least partially gelled hydrogel 102 using the absorbent paper 114 applied to the at least partially gelled hydrogel outside of the needle.

In order to prevent movement of the dense hydrogel 100 in the needle once the densification process is almost complete, the first valve 120 is opened and the second valve 122 is closed. This closes the pathway 123 to the pump 106 while providing an open path through the first valve 120 in order to equalize the pressure within, and surrounding the capillary 104.

Optionally, for controlled election of the densified gel 100, the pathway 123 between the dense hydrogel and the pump may be flooded with a less-compressible fluid than air, such as liquid. A syringe 130 containing a liquid (e.g. water, phosphate buffered saline, cell culture medium, saline etc) is connected to the second valve 122 whilst a pathway towards the needle 104 is closed and the pathway 123 is open. The liquid from the syringe 130 can then replace the air. Once the pathway 123 is full of liquid, the pathway towards the syringe 130 is closed, and the pathway to the needle 104 is opened. Positive pressure can then be applied by the pump 506 to elect the dense gel 100.

Depending on the size of the dense hydrogel, and diameter (i.e. gauge) of the needle, the required election pressure will vary. In one example, a 1 mL with a 10G (2.692 mm internal diameter) needle requires between 1-1.5 ATM, while a 16G (1.194 mm internal diameter) needle can require up to 2 ATM.

Figure 6:
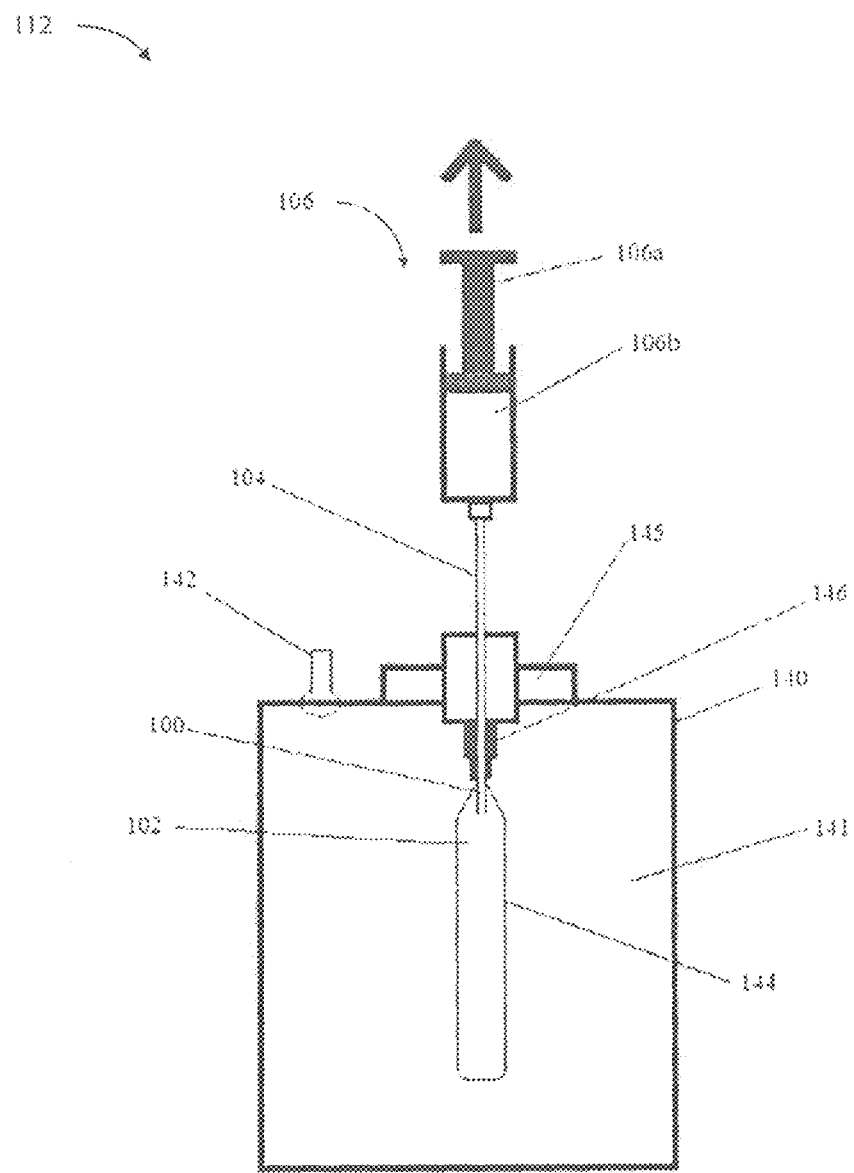
FIG. 6 illustrates certain embodiments of the system of FIG. 2b for producing dense hydrogels.

Referring now to FIG. 6, an embodiment of the method and system of FIG. 2b is shown, in which positive pressure is applied directly to the uncompacted at least partially gelled hydrogel 102 by a driver 106. The driver in this embodiment, is a chamber 140 for receiving the at least partially gelled hydrogel 102 or the hydrogel precursor, the chamber 140 having pressurizable environment 141. The environment 141 can be any substance which can be pressurized. The system 112 further comprises an inlet 142 through which the environment 141 can be pressurized such as by forcing in gas or liquid to provide a positive pressure on the partially gelled hydrogel 102. In certain embodiments, the partially gelled hydrogel 102 is separated from the environment by a flexible membrane 144. In certain embodiments, the membrane 144 is a semi-permeable membrane which allows the flow of fluid from the at least partially gelled hydrogel to the environment. The membrane 144 can be an osmotic membrane (e.g. dialysis tubing). This membrane 144 is attachable to the chamber via an attachment 146, such as a threaded male and female attachment, that can clamp the membrane 144 in the correct position for attachment to the capillary 104. The environment 141 can include a hypertonic medium (not shown) surrounding the membrane 144 and the least partially gelled hydrogel 102 contained therein. The hypertonic medium acts as the removal means 114 for removing liquid from the partially gelled hydrogel.

To increase the rate of insertion of the at least partially gelled hydrogel 102 into the capillary 104, the pressure difference between the internal and external environment of the capillary can be controlled. In this embodiment, negative pressure across the capillary can be generated by the driver 106 which can be a syringe apparatus (syringe piston 106a actuating in a syringe chamber 106b) or a vacuum pump (not shown). The capillary 104 extends through a top wall of the chamber 140. An attachment/seal 145 may be provided to attach and/or seal the capillary to the chamber 140. The attachment 145 may be a locking screw.

The positive pressure within the chamber 140 can be generated by the influx of any substance, such as gas through the inlet 142. In certain embodiments, gas is pumped into the chamber 140 which in turn applies pressure on the fluid (e.g. hypertonic media) contained within the chamber 140, which in turn applies pressure on the at least partially gelled hydrogel 102 to force it into the capillary 104. The difference in pressure between the external and internal environments of the capillary may permit large samples of the at least partially hydrated hydrogel to be compacted to a greater extent than the embodiments shown in FIGS. 3 and 5. By means of the chamber 140 and membrane 144, a sterile environment can be achieved without the loss of material including additives in the partially gelled hydrogel (such as therapeutic agents, cells, particles, etc.). Furthermore, removal of the water from the at least partially gelled hydrogel 102 through osmosis as it is pressed into the capillary 104 can also shorten the time to make the dense hydrogel.

Figure 7:
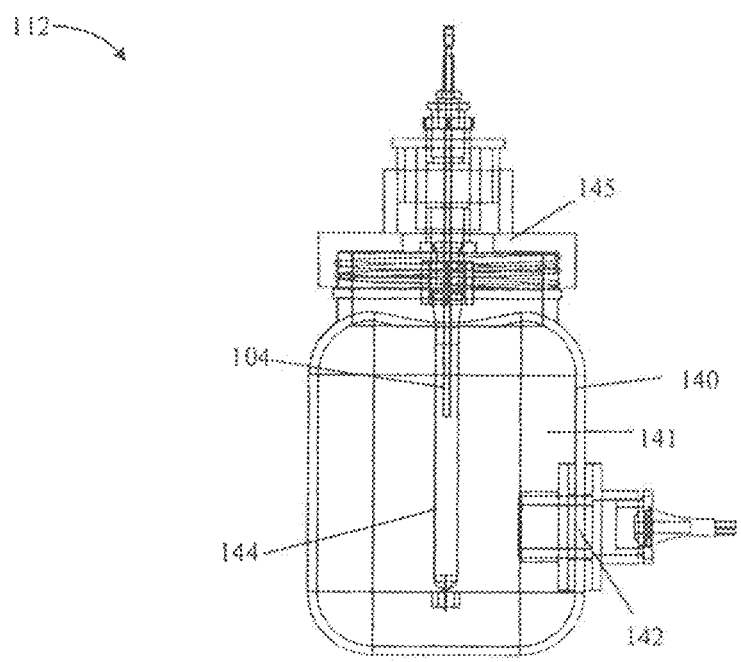
FIG. 7 is a three-dimensional view of an alternative embodiment of the system of FIG. 6.
Figure 8:
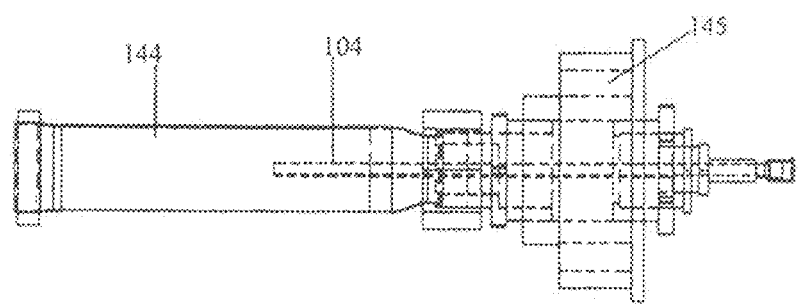
FIG. 8 is an enlarged view of a capillary portion of the system of FIG. 7.

FIGS. 7 and 8 illustrate in more detail an embodiment of the system of FIG. 6.

In any of the abovedescribed embodiments of the system or method of the present disclosure, a stepped approach may be taken to obtain a dense hydrogel with small diameters, in which the at least partially gelled hydrogel is first compacted in a larger internal diameter capillary, followed by further compaction in a capillary or capillaries with a smaller internal diameter. This approach can avoid or minimize clumping or loss of gel functionality. In this case, the capillaries may be separate or joined.

According to another aspect of the present disclosure (illustrated in FIGS. 6 and 7), there is provided a device for preparing a dense hydrogel, the device comprising the chamber 140 for receiving the at least partially gelled hydrogel 102 or a hydrogel precursor; the connector (attachment) 145 for connecting to a capillary 104 into which the at least partially gelled hydrogel 102 can be driven to form a dense hydrogel 100; the inlet 142 connectable to a pump for applying positive pressure in the chamber 140.

From a further aspect, there is provided a device tor preparing a dense hydrogel, the device comprising: a membrane 144 for receiving an at least partially gelled hydrogel 102 or a hydrogel precursor, wherein the membrane 144 has flexible walls, and the connector 145 for connecting to the capillary 104 into which the at least partially gelled hydrogel 102 can be forced to form a dense hydrogel 100; the chamber 140 for receiving the membrane 144 and for applying pressure to the flexible walls, in use, to force the at least partially gelled hydrogel 102 into the capillary 104. The chamber 140 further comprises the inlet 142 for pressurizing the environment 141. The flexible walls of the membrane 144 comprise an osmotic membrane, and the chamber 140 comprises a hypertonic medium in contact with the osmotic membrane for removing water from the at least partially gelled hydrogel by osmosis. The device further comprises a pump for exerting pressure across the capillary.

The device, system or method of FIG. 6 or 7 can further comprise a heat and/or humidity controller for controlling the heat and/or humidity inside the chamber 140. This can regulate the gelling process. The device further comprises the capillary 104, the capillary 104 having a smaller diameter than the diameter of the chamber or the vessel.

According to another aspect of the present disclosure, there is provided a kit for forming a dense hydrogel, the kit comprising a capillary 104 having a bore 105, and a driver 106 attachable to an end of the capillary for driving an at least partially gelled hydrogel into the bore 105 of the capillary to form a dense hydrogel. The kit further comprises any of the system 112 or device features described above and illustrated in the figures. In certain embodiments, the kit comprises a hydrogel precursor or an at least partially gelled hydrogel. The hydrogel precursor can be a collagen hydrogel precursor, such as type I collagen solution. The capillary is a needle with a bore. The driver can be a pump (e.g. as illustrated in FIG. 5), a syringe (e.g. as illustrated in FIGS. 3 and 4), or a positive pressure driver (e.g. the pressurized chamber 140 of FIGS. 6 and 7). The kit can further include instructions for use.

According to another aspect of the present disclosure, there is provided dense gels having aligned fibrils. The dense hydrogel may have a substantially aligned solid phase, and the density of the solid phase may be from about 2 to about 60 wt %. In certain embodiments, the hydrogel is dense collagen with a density of from about 2 to about 60%, about 5 to about 50%, about 5 to about 45%, about 10 to about 40%, about 15 to about 35%, about 20 to about 30%, about 5 to about 60%, about 10 to about 60%, about 15 so about 60%, about 20 to about 60%, about 25 to about 60%, about 30 to about 60%, about 35 to about 60%, about 40 to about 60%, about 45 to about 60%, or about 30 to about 60%. The solid phase of the hydrogel is fibrillar and the alignment of the fibers is >0.038 unit when measured using the method reported by Ayres et al. [Ayres et al., Biomaterials, 2006, 27(52): 5524-5534; and Ayres et al., J. Biomater. Sci. Polymer Edn, Vol. 19, No. 5, pp. 601-621 (2008)]. The dense collagen is suitable for injection into a treatment site of a patient and has an internal diameter corresponding to or less than a diameter of a needle or a catheter. In this embodiment, the collagen further includes cells or particles. The cells are aligned with the aligned fibrils. In other embodiments, the particles are fibroin-derived polypeptides, such as polypeptides isolated and extracted from silk fibroin such as a soluble fraction Cs, a precipitated fraction Cp, or a combination of the Cs and Cp fractions.

EXAMPLES

The examples below are given so as to illustrate the practice of various embodiments of the present disclosure. They are not intended to limit or define the entire scope of this disclosure.

Example 1

Morphological Analysis of Dense Aligned-Fibrillar Collagen Gels

Dense collagen hydrogels were made according to certain embodiments of the present disclosure substantially as illustrated in, and described in relation to, FIG. 3. The collagen fibre alignment in the resultant dense hydrogels was investigated using Scanning Electron Microscopy and polarized attenuated total reflectance Fourier transform infrared (ATR-FTIR) spectroscopy.

For SEM, the dense gels were fixed with a 4% glutaraldehyde 0.1M sodium cacodylate solution overnight at 4° C. The samples were then washed with deionised distilled water and dried at 4° C. through a graded series of ethanol solutions, in order to maintain collagen triple helical structure, samples were subsequently dried with a Ladd critical point dryer. Samples were then sputter corned with Au/Pd. The SEM analysis was performed with a S-4700 Field Emission-STEM as 2 kV and 10 µA. For ATR-FTIR, a FTIR microscope was coupled wish a polarizer. The incident infra-red light was rotated 90° on a spot size of 100 µm$^2$ and an average (n=64) spectrum of the sample was acquired as 0° and 90° using a resolution of 4 cm$^{-1}$.

Figure 9A:
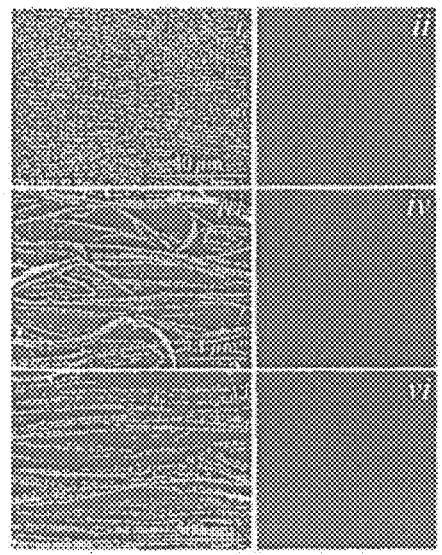
FIG. 9a are SEM micrographs (left column) and corresponding last Fourier-transform (FFT) images (right column) showing increasing magnifications of the nanofibrillar structure of dense collagen gels according to certain embodiments of the present disclosure (Example 1).
Figure 9B:
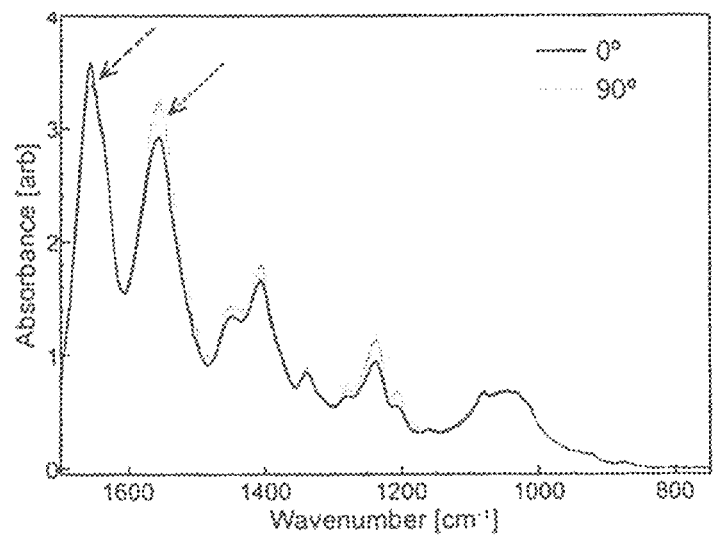
FIG. 9b is a polarized FTIR spectrum of the dense collagen gels of FIG. 9a illustrating a change in the absorbance of the Amide I and II according to the polarization of the infra-red light.

It can be seen in FIG. 9a that the dense collagen hydrogel has substantially aligned collagen fibrils. Driving the nondensified partially-gelled collagen gel into a capillary forces the collagen fibrils to re-arrange and to align with one another along the long axis of the capillary. The collagen fibrillar density of the dense hydrogels was found to be from about 2 to about 60 wt %. The left column of FIG. 9a shows the collagen fibrils at increasing magnifications. The right column shows the Fast Fourier Transform (FFT) of the images. When analyzed according so the method reported by Ayres et al. (see above), a degree of anisotropy of 0.053±0.012 was reached. The vertical light gray lines are an indication of the alignment. Polarized ATR-FTIR spectra of injectable collagen gels taken by rotating the collimator by 90° (FIG. 9b) showed how the collagen is not denatured by the whole process (Amide I peak at 1661 cm−1). In addition, the reduction of the Amide I absorbance and the corresponding increase of the Amide II absorbance with a 90° shift in the polarization of the IR light corroborated the morphological analysis, as it is an indication of the alignment of the collagen fibrils.

Example 2

Incorporation of Anionic Fibroin Derived Polypeptides Into the Dense Aligned-Fibrillar Collagen Gel Dense collagen hydrogels incorporating anionic fibroin derived polypeptides were made according to certain embodiments of the present disclosure substantially as illustrated in, and described in relation to, FIG. 3. This illustrates that the presently disclosed system 112 and method can be used so incorporate any macromolecules or inorganic materials, such as particles, fibrils, hollow fibrils, having a size between about 5 nm to about 300 µm, into the dense hydrogel.

In this example, collagen precursors were hybridized with 10 dry wt % anionic fibroin derived polypeptides (Cs) at the point of fibrillogenesis (fibril formation). This was then passed into a 0.9 mm capillary needle according to certain embodiments of the present disclosure to form a dense collagen-Cs hybrid gel. The dense collagen-Cs hybrid gels were then injected into sterile simulated body fluid (SBF) at 37° C. for up to 7 days to investigate the bioactivity of the hybrid material, in comparison to the previously published data of the inventors (Marelli et al. Biomaterials, 2012; 33:102-8, the contents of which are incorporated herein by reference).

Figure 10A:
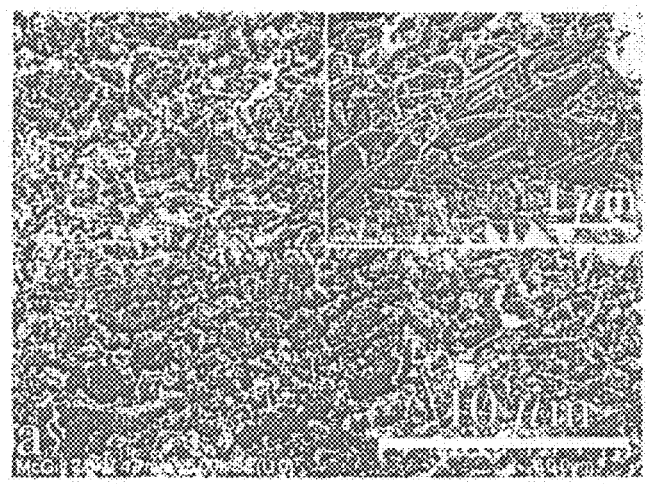
FIG. 10a is a scanning electron micrograph of a dense collagen gel hybridized with anionic fibroin derived polypeptides (Cs) in simulated body fluid, according to certain embodiments of the present disclosure (Example 2).
Figure 10B:
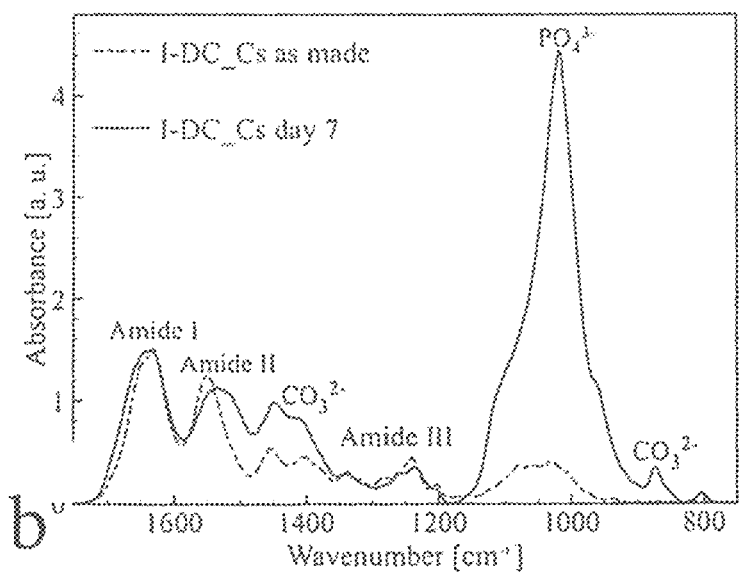

It was found that the method of densifying the hydrogel did not affect the mineralization of the dense collagen gels in SBF as at day 7 carbonated-hydroxyapatite was extensively formed within the aligned collagenous matrix. As seen in FIG. 10a, the collagenous matrix maintained its nanofibrillar aligned structure throughout the process and resulted in homogenous mineralization. The inset image in FIG. 10a is a higher magnification micrograph in which the collagen nanofibrils and carbonated-hydroxyapatite crystals are visible. The exposure of this dense collagen gel to SBF resulted in the rapid mineralization of the aligned collagenous matrix. As can be seen in the FTIR spectra of FIG. 10b, $v_3$ and $v_1$ $PO_4^{3-}$ absorbances at 1012 cm$^{-1}$ and 961 cm$^{-1}$ together with the $v_2$ $CO_3^{2-}$ absorbance at 871 cm$^{-1}$ indicated the formation of carbonated hydroxyapatite within the anisotropic collagen matrix.

Example 3

Viability of Cells Seeded Within the Dense Aligned-Fibrillar Collagen Gels

Cells were incorporated in the at least partially gelled hydrogel before being passed into the capillary, according to certain embodiments of the present invention, and were found to remain viable through the densification and fibrillar alignment process.

Figure 11:
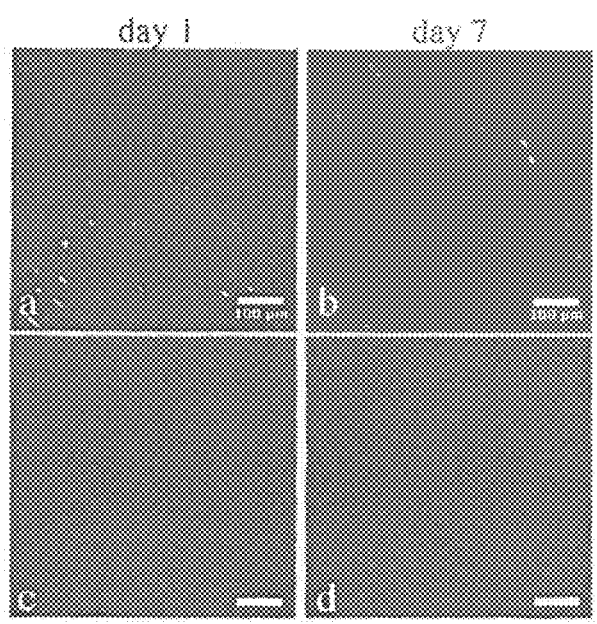
FIG. 11 illustrates the early response of NIH/3T3 fibroblasts to dense collagen gel formation process according to certain embodiments of the present disclosure (Example 3) through confocal laser scanning microscopy (CLSM) obtained with (a,b) Calcein AM-Ethidium Bromide and (c,d) F-actin staining of NIH/3T3 at day 1 left column) and day 7 (right column).

NIH/3T3 cells were homogenously seeded in dense collagen gels by incorporating them in the collagen solution at the point of gel self-assembly. The method and system of FIG. 3 was applied. NIH/3T3 cells seeded in the dense collagen gels were cultured up to day 7 in basal culture medium. Viability and morphological analysis of NIH/3T3 cells seeded in injectable dense collagen gels are presented in FIG. 11. The top and bottom rows show, respectively, confocal laser scanning microscopy (CLSM) images obtained with (a,b) Calcein AM-Ethidium Bromide and (e,d) F-actin staining of NIH/3T3 at days 1 (left column) and 7 (right column). At day 1, the NIH/3T3 cells seeded in dense collagen were alive and aligned along the nanofibrils. At day 7, viability and alignment of the NIH/3T3 cells were maintained.

Example 4

Neuronal Transdifferentiation of Mouse Mesenchymal Stem Cells Seeded Within Dense Aligned-Fibrillar Collagen Gels Mouse mesenchymal stem cells (m-MSCs) were incorporated in the at least partially gelled hydrogel (at the point of self-assembly) before being passed into a 0.9 mm diameter capillary to form a dense aligned-fibrillar collagen gel according to certain embodiments of the present invention (FIG. 3) ("I-DC"). The transdifferentation of the m-MSCs in the dense gels toward a neuronal plenotype was then investigated (Table 1) by culturing the MSCs in the dense collagen gels and exposing them to neural transdifferentiation media, and comparing them to a control.

Culturing comprised placing the I-DC gels in complete media (alpha-minimal essential media, 10% HyClone Foetal Bovine Serum, 2 mM L-glutamine, 100 U/ml, Penicillin-Streptomycin containing differentiation (diff) supplements conducive towards nervous (N−) lineage. For N-diff, 1 mM Beta-mercaptoethanol was supplemented to the culture media for the first day, and 35 ng/mL of all-trans-retinoic acid supplemented the media for the second day. In subsequent days, only 5 µM forskolin, 10 ng/mL basic fibroblast growth factor, platelet derived growth factor (AA) 10 ng/mL, and 10 ng/mL insulin-like growth factor-1 were supplemented to the media (which was changed every other day).

The control was m-MSCs seeded dense collagen gels without fibrillar alignment ("DC"). The control gels were made by neutralizing 3.2 ml of rat tail tendons type I collagen (2.11 mg/ml, in 0.6% acetic acid) with 0.8 ml of 10 times concentrated Dulbecco Modified Eagle Medium (10× DMEM) and 37 µm of 5M NaOH. The solution (4 ml) was then cast in a rectangular mould (19×43 mm$^2$) and incubated at 37° C. for about 23 minutes. m-MSCs were incorporated at the point of self-assembly. The gel was then gently removed from the mould and compressed to form rectangular sheets using 1 kPa for 5 minutes in combination with blotting. The sheets were rolled along the long axis and halved to give cylindrical shaped dense collagen specimens incorporating MSCs of 1.0±0.1 mm diameter.

mRNA expression of each gene was first normalized by a stable housekeeping gene (m-mEef2) and then related so the normalized expression level of the same gene in MSCs seeded in dense collagen gels (I-DC) at day 1. The up-regulation of all the neural genes used as market for neuronal phenotype indicated an accelerated transdifferentiation of MSCs cells towards the neuronal phenotype already at day 1 of culture. The markers were then upregulated for the culture time points considered.

Figure 12A:
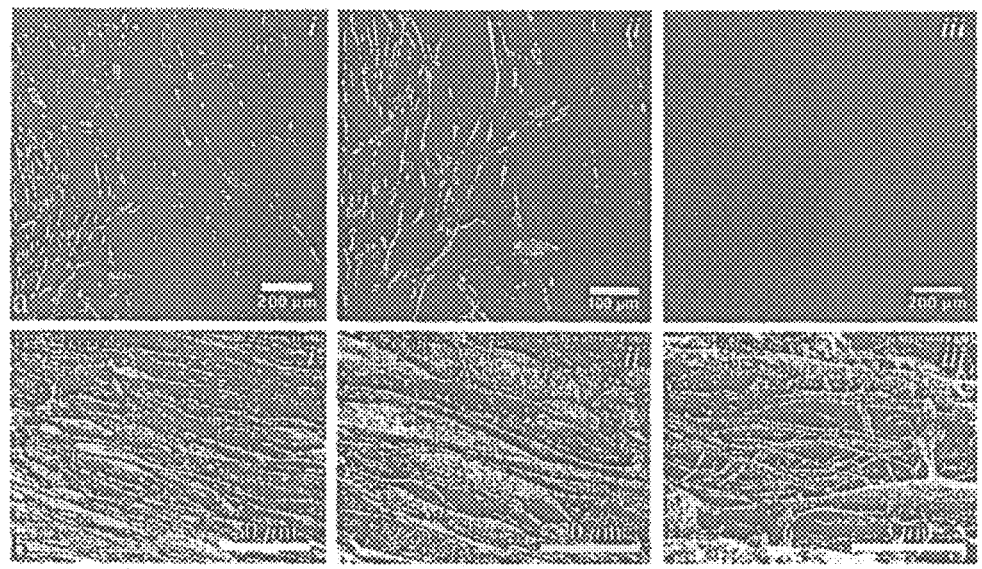
FIG. 12a illustrates neural transdifferentation of mouse Mesenchymal stem cells (m-MSCs) cultured in dense collagen gets ("I-DC") according to certain embodiments of the present disclosure and exposed to neural transdifferentiation media (Example 4) viewed by: top row: a) confocal laser scanning microscopy (CLSM) with i Calcein-AM green positive staining, ii Ethidium Bromide red binding cells, and iii F-actin fibers staining in red), and bottom row: scanning electron micrographs of the I-DC gel at different magnifications.

The dense collagen gels according to embodiments of the present disclosure (I-DC) supported the culture and the transdifferentiation of the m-MSCs toward a neuronal phenotype. The cells remained viable at all time points (FIG. 12a, see top row (a: i and ii), with an elongated cysoskeleton along the fibril direction (FIG. 12a, see top row a: iii) and displayed a typical dome-shaped nucleus typical of the neuronal phenotype (FIG. 12ai, see bottom row b) when analyzed through confocal latter scanning microscopy (CLSM) and SEM. The m-MSCs cultured in dense collagen gels for 14 days showed preferential alignment along the aligned collagen fibrils. In the control gels, the cells appeared to be more rounded in nature (less-oriented). These results showed that I-DC provided a better environment to sustain the transdifferentiation of m-MSCs toward a neuronal phenotype, when compared to the DC control.

Figure 12B:
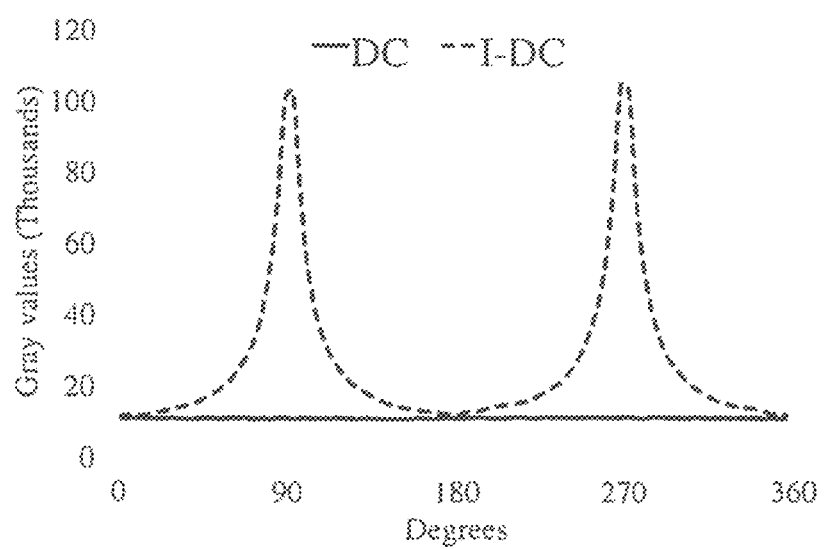
FIG. 12b shows fast Fourier transform-based power density spectra of the m-MSC cells within the I-DC gets (dashed line) and a control dense collagen with non-aligned fibrils and M-MSC cells ("DC") (solid line) of FIG. 12a at day 21 of culture, as an indication of m-MSC cell elongation and alignment.

FIG. 12b is a fast Fourier transform-based power spectra density of the m-MSCs distribution within the I-DC gels (dashed line) and the DC control gel (solid line) at day 21 of culture. The power spectra density were obtained from the CLSM microscopy images according to Millet et al., Integr. Biol., 2011, 3, 1167-1178. This provides a qualitative evaluation of cell elongation and alignment. The tight radial distribution and the highly increased gray value of m-MSCs around 90° and 270° cultured in I-DC gels when compared to the DC counterpart is an indication of their elongated structure and of their high degree of alignment within the aligned hydrogel of the present disclosure.

Figure 13:
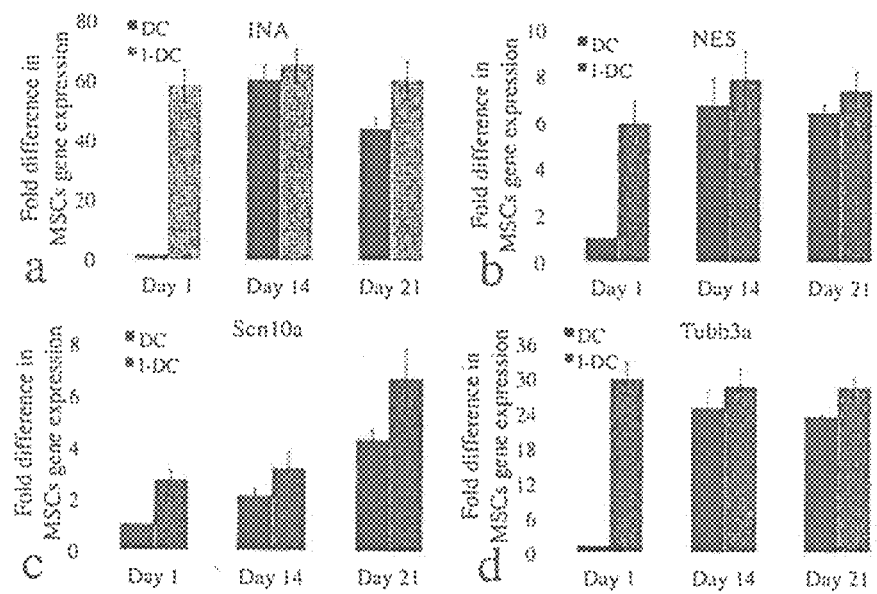
FIG. 13 illustrates the gene expression of the m-MSCs is the I-DC gels of FIG. 12a compared to control DC gels.

In addition, q-PCR analysis of the m-MSCs gene expression evidenced an over-expression of neuronal-like genes in I-DC collagen, when compared to the control DC (FIG. 13), indicating that the I-DC gels were better able to support the neuronal transdifferentiation of the m-MSCs cells. The anisotropic matrix of the dense collagen gels of the present disclosure appears to make it a more stimulating environment for neuronal cells when compared to the control. Together these results suggested that the dense collagen gels of the present disclosure may be suitable constructs for nerve regeneration, as well as other applications in which aligned cells or other agents are preferred. These constructs may be injectable.

TABLE 1

Primers (In 5'→ 3' Orientation) used to investigate the transdifferentiation of MSCs toward a neuronal phenotype in 1-DC and DC gels

| | |
|---|---|
| Eef2 | (+) GCTGCACAGTGCCCACCCAT |
| | (−) CACAGCCTGCCAGTCCAGC |
| NES | (+) CCAGCTGGCTGTGGAAGCCC |
| | (−) TGTGCCAGTTGCTGCCCACC |
| INA | (+) AGACGCGGTTTAGCACCGGC |
| | (−) GGACAGCCCGGCAGAGGAGA |
| Sen10a | (+) GGGAGAGCCCTCGGGTCCCTG |
| | (−) GTTTTGCGCACCTGCCAGCC |
| Tubb3a | (+) TACACGGGCGAGGGCATGGA |
| | (−) TCACTTGGGCCCCTGGGCTT |

Example 5

Osteoblastic Differentiation of Mouse Mesenchymal Stem Cells Seeded Within Dense Aligned-Fibrillar Collagen Gels Mouse mesenchymal stem cells (m-MSCs) were seeded in collagen gels at the point of self-assembly and dense gels were then produced according to embodiments of the present disclosure using a 0.9 mm diameter capillary to form the dense hydrogel. The differentiation of m-MSCs in the dense gels toward an osteoblastic phenotype was then investigated and compared to MSCs seeded and cultured in control gels (the control gels were made as described above in Example 4). Osteoblastic differentiation supplements were used comprising 50 µg/mL ascorbic acid, 50 mM beta-glycerophosphate, and 1 µM betamethasone, with replenishment every 3 days.

Figure 14A:
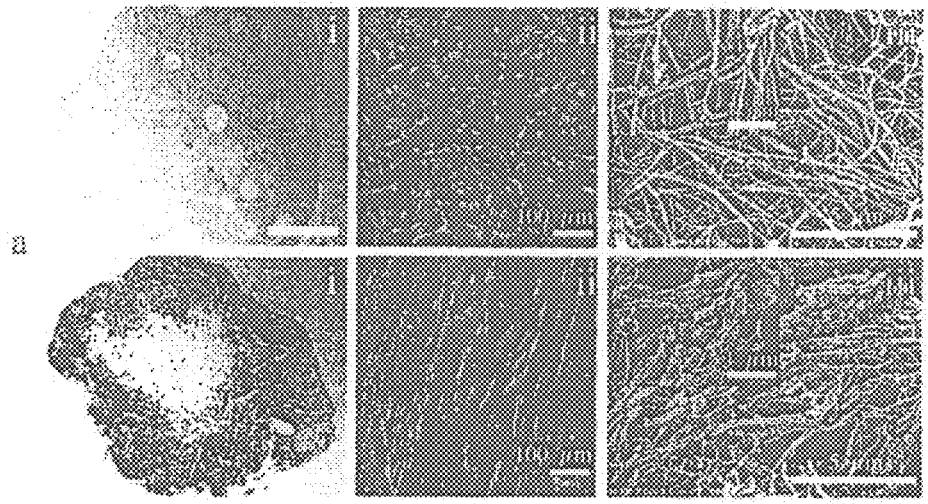
FIG. 14a illustrates osteoblastic differentiation of MSCs cultured within dense aligned-fibrillar collagen gels in osteogenic media according to certain embodiments of the present disclosure ("I-DC") (bottom row) compared to a control comprising m-MSCs cultured within dense collagen gels with no fibrillar alignment ("DC") (top row), as investigated at day 21 of culture by (i) Von Fossa stained histological sections (scale bar=500 µm), (ii) CLSM (Calcein-AM green positive staining and Ethidium Bromide red binding cells), and (iii) SEM (Example 5).

The dense collagen gels of the present invention (I-DC) supported the culture of m-MSCs and accelerated their differentiation toward an osteoblastic phenotype, when compared so conventional DC gels (no fibrillar alignment). For all the time points considered, the m-MSCs remained viable (FIG. 14a bottom row (i, ii), and were found to mineralize the aligned collagen matrix (FIG. 14a bottom row (iii)), when analyzed through Von Kossa staining of histological sections, CLSM and SEM. The I-DC gels showed a greater extent of mineralization which is a sign of scaffold-induced accelerated osteoblastic differentiation. The mineral phase was seen within the outer region of the dense collagen gel. The CLSM staining (Calcein-AM green positive staining and Ethidium Bromide red binding cells) showed cells aligned along the collagen nanofibril direction for I-DC. For the control DC gels, a random cell distribution was seen.

SEM allowed an investigation of the mineralization of the collagenous matrix. For the I-DC, a mineralized collagen matrix was observed within aligned fibrils (FIG. 14 a, bottom row (iii)). For the DC gels, a sporadic presence of mineral phase nucleated on collagen was observed (FIG. 14 a, top row (iii)).

Table 2 summarizes the extent of mineralization seen in the I-DC and DC samples. In particular, Von Kossa stained histological sections taken at day 21 (FIG. 14 i) revealed an extensive mineralization of I-DC gels (48±19% of positively stained scaffold surface), when compared to DC gels (7±4% of positively stained scaffold surface).

TABLE 2

Mineralization score of I-DC and DC gels. The score is based on % of area of histological sections of I-DC and DC gels that was mineralized as viewed by Von Kossa staining.

| | Day of culture of m-MSCs in I-DC or DC gels | |
|---|---|---|
| | Day 14 | Day 21 |
| DC | + | + |
| I-DC | ++ | +++ |

+: 0-17% of area was mineralized; ++: 18-34% of area was mineralized; +++: 35-51% of the area was mineralized.

Figure 14B:
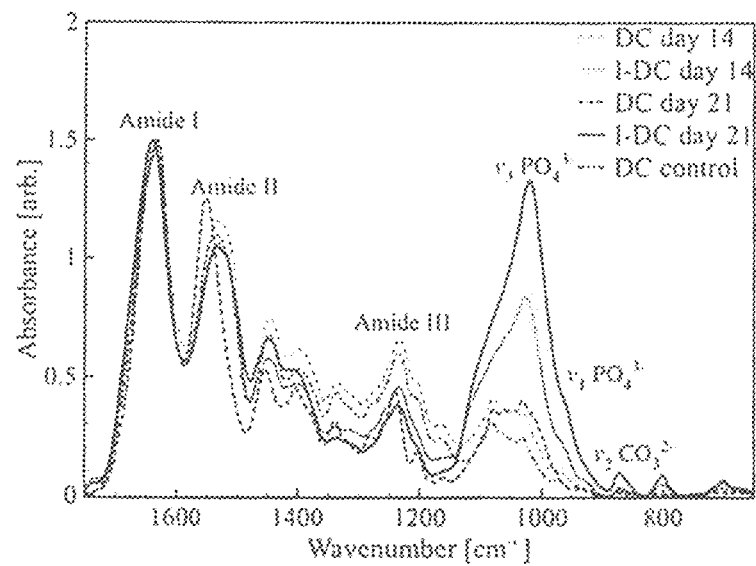
FIG. 14b is an ATR-FTIR spectrum of the I-DC and DC gels of FIG. 14a at days 14 and 21 of culture.
Figure 14C:
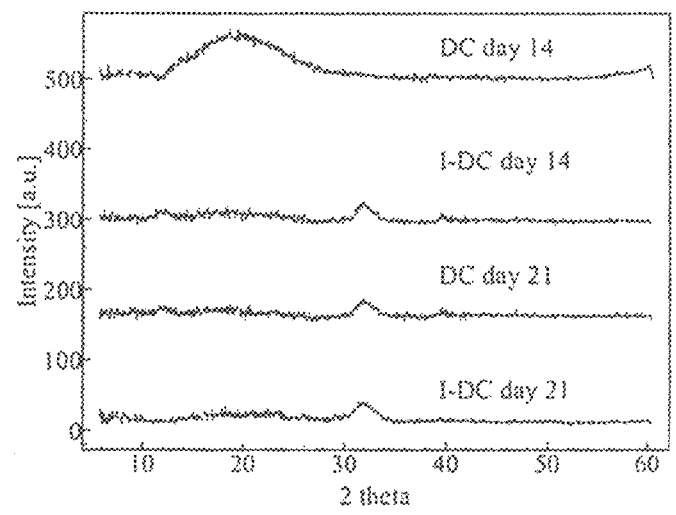
FIG. 14c is an x-ray diffraction spectrum of the anisotropic I-DC collagen gels of FIG. 14a displaying an accelerated formation of apatite (more pronounced peak around 31° C.) at days 14 and 21 in culture, when compared to isotropic DC gels used as control.

In addition, ATB-FTIR and XRD analyses were used to evaluate the MSC-mediated mineralization of the DC and I-DC gels. In FIG. 14b, MSC-seeded DC and I-DC gels showed an increase in the absorbance of $v_3$ $PO_4^{3-}$ at 1018 cm$^{-1}$ and of $v_1$ $CO_3^{2-}$ at 872 cm$^{-1}$, suggesting the formation of carbonated hydroxypapatite. FTIR spectra of I-DC gels showed a higher absorbance of the $v_3$ $PO_4^{3-}$ vibration at days 14 and 21 when compared to the DC ones, indicating an accelerated mineralization of the injectable dense collagen gels.

XRD diffractographs of MSCs-seeded DC and I-DC at day 14 and 21 (FIG. 14c) showed more crystalline structures in the I-DC gels, due to the preferential alignment of the collagenous nanofibrils within the gel structure. At day 14, the formation of an apatitic phase (broad peak around 31°) was visible in I-DC but not in DC gels, indicating an accelerated mineralization of the injectable dense collagen gels when compared to the DC counterpart.

Figure 14D:
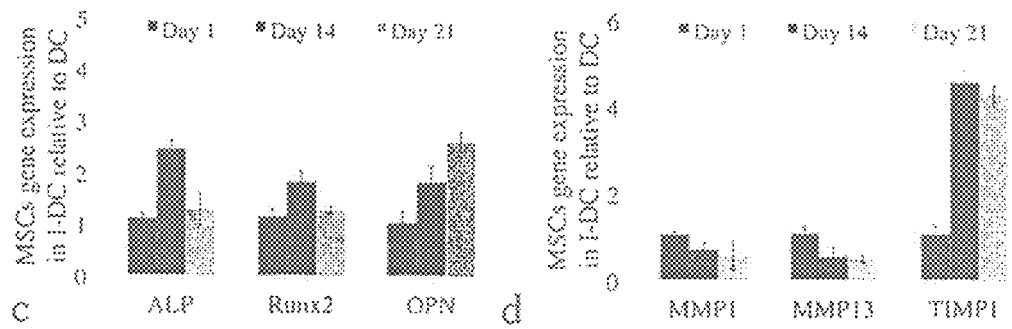
FIG. 14d shows changes in ALP, Runx2 and OPN (left side) and in MMP1, MMP13 and TIMP1 (right side) gene expression within the I-DC gels of FIG. 14a at days 1, 14 and 21 relative to the DC gel control of FIG. 14a at day 1.

FIG. 14d shows changes in ALP, Runx2 and OPN (left side) and in MMP1, MMP13 and TIMP1 (right side) gene expression within I-DC at days 1, 14 and 21 relative to DC at day 1 to evaluate the osteoblastic differentiation of MSCs. At each time point, RNA expression of each gene was first normalized by the housekeeping gene (GAPDH) and then related to the normalized expression level of the target gene in I-DC. Two-way ANOVA test (coupled with Tukey's test, $p<0.05$) was used to evaluate the effects of material and culture time on MSCs gene expression. Both material and culture time significantly affected ($p<0.05$) the expression of ALP, Runx2 and OPN genes. ALP, Runx2 and OPN genes were upregulated in MSCs cultured in I-DC gels when compared to the DC counterpart both at days 14 and 21 ($p<0.05$), indicating an accelerated osteoblastic differentiation of MSCs in I-DC gels. At day 21, the downregulation of ALP and Runx2, early markers for the osteoblastic differentiation of MSCs and the up-regulation of OPN, a marker for mature osteoblastic differentiation, indicated that I-DC were able to sustain the osteoblastic differentiation of MSCs toward a more mature cell type.

Both material and culture time significantly affected ($p<0.05$) the expression of MMP1, MMP13 and TIMP1 genes. MMP1 and MMP13 were downregulated in MSCs cultured in I-DC gels when compared to the DC control both at days 14 and 21 ($p<0.05$). TIMP1 was upregulated in MSCs cultured in I-DC gels when compared to the DC control both at days 14 and 21 ($p<0.05$). The downregulation of genes for the synthesis of metalloproleases (MMPs), together with the upregulation of genes for encoding MMPs inhibitor suggested a significant reduction in the MSCs-mediated remodeling of the aligned dense collagenous matrices.

Together these results suggest that the dense gels of the present disclosure may be suitable as constructs for bone regeneration. Also, due at least in part to the dimensions of the dense aligned-fibrillar hydrogel obtained, these resultant hydrogels may be injectable. In addition, the anisotropic matrix of the dense gels of the present disclosure accelerated the cell-mediated mineralization of the gels.

Example 6

Figure 15:
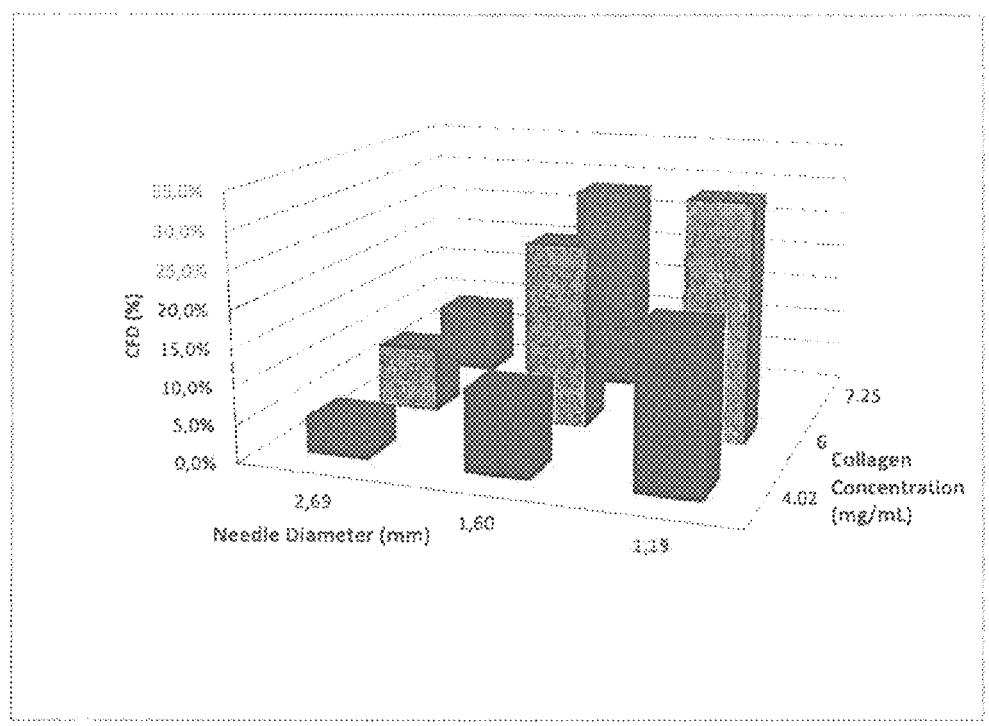
FIG. 15 is a graph illustrating the variation of the density of the resultant dense hydrogel by varying the capillary diameter and hydrogel precursor solution concentration (Example 6).

Controlling the Density of the Resultant Dense Hydrogen by Varying Capillary Diameter, Hydrogel Precursor Solution Concentration and Applied Pressure Differential Using the system and method described in FIG. 5, the final collagen fibre density (CFD) of various initial concentrations of collagen gel precursors and needle diameters were investigated. As shown in FIG. 15, it was found that decreasing the capillary diameter increased the resultant hydrogel CFD, where Gauge 10=2.69 mm, Gauge 14=1.60 mm, and Gauge 16=1.19 mm. Increasing the collagen precursor solution concentration also increased the resultant hydrogel CFD. The system and method embodiments of FIG. 5 generally applied a higher pressure differential than the embodiments of FIG. 3. Higher resultant CFD values were observed in the embodiments of FIG. 5. Increasing the pressure differential even further (as is the case for the embodiments illustrated in FIGS. 6-8), or the initial starting concentration, would further increase the resultant CFD.

While several embodiments of the invention have been described herein, it will be understood that the present invention is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention as defined in the appended claims.

The invention claimed is:

1. A method for preparing a dense hydrogel, the method comprising:
    providing a gelled hydrogel comprising a three-dimensional network of a solid phase in a liquid phase;
    placing the gelled hydrogel in fluid communication with a first end of a capillary; and
    driving the gelled hydrogel into the capillary to form a dense hydrogel in the capillary, a percentage of the solid phase in the dense hydrogel being higher than a percentage of the solid phase in the gelled hydrogel, the driving the gelled hydrogel into the capillary comprising applying a negative pressure on the at gelled hydrogel through a second end of the capillary, or applying a negative pressure on the dense hydrogel in the capillary through the second end of the capillary.

2. The method of claim 1, wherein driving the gelled hydrogel into the capillary comprises applying a pressure differential between the capillary and the gelled hydrogel.

3. The method of claim 1, further comprising removing liquid from the gelled hydrogel before, or at the same time as, driving it into the capillary.

4. The method of claim 1, further comprising providing a hydrogel precursor and initiating gelling of the hydrogel precursor to form the gelled hydrogel.

5. The method of claim 1, wherein the gelled hydrogel is at least one of collagen, hyaluronan, chitosan, fibrin, gelatin, alginate, agarose, polyacrylamide, poly(ethylene glycol) (PEG), polyacrylic acid (PAA), hydroxy ethyl methacrylate (HEMA), and combinations of the same.

6. The method of claim 1, further comprising adding at least one bioactive agent to the gelled hydrogel before or during a gelling step, wherein the at least one bioactive agent is selected from cells, genes, drug molecules, therapeutic agents, particles, osteogenic agents, osteoconductive agents, osteoinductive agents, anti-inflammatory agents and growth factors.

7. The method of claim 1, further comprising ejecting the dense hydrogel from the capillary.

8. The method of claim 1, wherein driving the at gelled hydrogel into the capillary further comprises exerting a positive pressure on the at gelled hydrogel.

9. The method of claim 8, wherein exerting the positive pressure comprises placing the gelled hydrogel in an environment which can be pressurized.

10. The method of claim 9, wherein the environment is air or liquid in a sealable container.

11. The method of claim 1, further comprising allowing a portion of the liquid phase of the gelled hydrogel to remain outside of the capillary whilst driving the gelled hydrogel into the capillary.

* * * * *